United States Patent
Loozen et al.

(10) Patent No.: US 7,335,659 B2
(45) Date of Patent: *Feb. 26, 2008

(54) SUBSTITUTED 10-ARYL-11H-BENZO[B]FLUORENES AND 7-ARYL-5, 6-DIHYDRO-BENZO[A]ANTHRACENES FOR SELECTIVE EFFECTS ON ESTROGEN RECEPTORS

(75) Inventors: Hubert Jan Jozef Loozen, Oss (NL); Markus Wagener, Oss (NL); Gerrit Veeneman, Oss (NL); Eduard Willem Zwart, Oss (NL)

(73) Assignee: N.V. Organon, Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/505,631

(22) PCT Filed: Feb. 14, 2003

(86) PCT No.: PCT/EP03/50018

§ 371 (c)(1),
(2), (4) Date: Aug. 19, 2004

(87) PCT Pub. No.: WO03/070675

PCT Pub. Date: Aug. 28, 2003

(65) Prior Publication Data

US 2005/0159405 A1  Jul. 21, 2005

(30) Foreign Application Priority Data

Feb. 22, 2002 (EP) .................. 02075727
Feb. 22, 2002 (EP) .................. 02075729

(51) Int. Cl.
| | |
|---|---|
| A61K 31/496 | (2006.01) |
| A61K 31/44 | (2006.01) |
| A61K 31/40 | (2006.01) |
| A61K 31/138 | (2006.01) |
| A61K 31/085 | (2006.01) |
| C07D 403/04 | (2006.01) |
| C07D 211/70 | (2006.01) |
| C07D 207/12 | (2006.01) |
| C07D 217/18 | (2006.01) |
| C07D 43/205 | (2006.01) |

(52) U.S. Cl. .............. 514/252.14; 514/279; 514/428; 514/651; 514/721; 544/295; 546/285; 548/528; 564/353; 568/633

(58) Field of Classification Search ............... None
See application file for complete search history.

(56) References Cited

U.S. PATENT DOCUMENTS

| | | | |
|---|---|---|---|
| 5,147,880 A | 9/1992 | Jones | 514/319 |
| 5,688,808 A | 11/1997 | Jones et al. | 514/285 |
| 6,686,371 B2 * | 2/2004 | Veeneman et al. | 514/284 |
| 6,756,375 B2 * | 6/2004 | Veeneman et al. | 514/238.8 |

FOREIGN PATENT DOCUMENTS

| | | |
|---|---|---|
| EP | 0 733 620 A1 | 9/1996 |
| EP | 0 785 191 A1 | 7/1997 |
| EP | 0 798 378 B1 | 10/1997 |

(Continued)

OTHER PUBLICATIONS

Singh et al., "Novel Mechanisms for Estrogen-Induced Neuroprotection," Exp. Biol. Med., vol. 231, pp. 514-521 (2006).*

(Continued)

*Primary Examiner*—Rebecca Anderson
*Assistant Examiner*—Jason M Nolan
(74) *Attorney, Agent, or Firm*—Susan Hess

(57) ABSTRACT

This invention provides a compound, or its possible salt, having the formula,

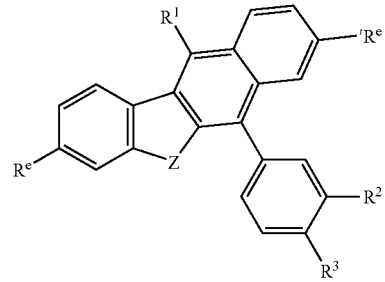

wherein: $R^e$ and $'R^e$ are OH, optionally independently etherified or esterified; Z is —$CH_2CH_2$— or —$C(R^4,R^5)$—, wherein $R^4$ and $R^5$ are independently H, (1C-2C)alkyl or form together a spiro(3C-5C)cycloalkyl; $R^1$ is H, halogen, $CF_3$, or (1C-4C)alkyl; $R^2$ and $R^3$ are independently H, halogen, —$CF_3$, —$OCF_3$, (1C-8C)alkyl, hydroxy, (1C-8C) alkyloxy, aryloxy, aryl(1C-8C)alkyl, halo(1C-8C)alkyl, —$O(CH_2)_mX$, wherein X is halogen or phenyl and m=2-4; —$O(CH_2)_mNR_aR_b$, —$S(CH_2)_mNR_aR_b$ or —$(CH_2)_mNR_aR_b$, wherein m=2-4 and wherein $R_a$, $R_b$ are independently (1C-8C)alkyl, (2C-8C)alkenyl, (2C-8C)alkynyl, or aryl, which alkyl, alkenyl and aryl can optionally be substituted with halogen, —$CF_3$, —$OCF_3$, —CN, —$NO_2$, —OH, (1C-8C) alkoxy, aryloxy, carboxyl, (1C-8C)alkylthio, carboxylate, (1C-8C)alkyl, aryl, aryl(1C-8C)alkyl or halo(1C-8C)alkyl; or $R_a$ and $R_b$ form a 3-8 membered ring structure, optionally substituted with halogen, —$CF_3$, —$OCF_3$, —CN, —$NO_2$, hydroxy, hydroxy(1C-4C)alkyl, (1C-8C)alkoxy, aryloxy, (1C-8C)alkylthio, carboxyl, carboxylate, (1C-8C)alkyl, aryl, aryl(1C-8C)alkyl, halo(1C-8C)alkyl.

11 Claims, No Drawings

FOREIGN PATENT DOCUMENTS

| EP | 0 832 881 A2 | 4/1998 |
|---|---|---|
| EP | 0 832 881 A3 | 4/1998 |
| EP | 0 873 992 A1 | 10/1998 |
| WO | WO 92/21661 A1 | 12/1992 |
| WO | WO 96/19458 A1 | 6/1996 |
| WO | PCT WO 01 72713 A | 10/2001 |
| WO | WO 01/72713 A1 * | 10/2001 |
| WO | PCT WO 02 16316 A1 | 2/2002 |

OTHER PUBLICATIONS

Usui, Pharmaceutical Prospects of Phytoestrogens, Endocrine J., vol. 53, Iss. 1, pp. 7-20 (2006).*

Arshad et al., "In Vitro Anti-Resportive Activity and Prevention of Ovariectomy-Induced Osteoporosis in Female Sprague-Dawley Rats by Ormeloxifene, A Selective Estrogen Recepor Modulator," J. Steroid Biochem. & Mol. Bio. 91, 67-78 (2004).*

Walf et al., "Administration of Estrogen Receptor Beta-Specific Selective Estrogen Receptor Modulators to the Hippocampus Decrease Anxiety and Depressive Behavior of Ovariectomized Rats," Pharmacol., Biochem. and Behavior (2006).*

Ishunina et al., "Estrogen Receptor α and Its Splice Variants in the Hippocampus in Aging and Alzheimer's Disease," Neurobiology of Aging (2006).*

Wallace et al., "Estrogen Receptor Modulators: Relationships of Ligand Structure, Receptor Affinity and Functional Activity," Current Topics in Med. Chem. 3, 1663-1680 (2003).*

Norman et al., Benzopyrants Are Selective Estrogen Receptor β Agonists Wtih Novel Activity in Models Benign Prostate Hyperplasia, J. Med. Chem. 49, 6155-6157 (2006).*

PCT Written Opinion of International Application No. PCT/EP03/50018 dated Feb. 11, 2004.

PCT International Preliminary Examination Report of International Application No. PCT/EP03/50018 dated May 12, 2004.

European Office Action for Application No. 03 706 624.8—2103 dated Mar. 11, 2005.

Mosselman, S. et al., "ERβ: identification and characterization of a novel human estrogen receptor," FEBS Letters, vol. 392 (1996) pp. 49-53.

* cited by examiner

SUBSTITUTED 10-ARYL-11H-BENZO[B]FLUORENES AND 7-ARYL-5, 6-DIHYDRO-BENZO[A]ANTHRACENES FOR SELECTIVE EFFECTS ON ESTROGEN RECEPTORS

The invention relates to a non-steroidal compound with selective affinity for estrogen receptors and to a method for selective estrogen receptor modulation (SERM) with such a compound and to the use of such a compound for the manufacture of a medicine for estrogen-receptor related treatments.

Compounds with affinity for estrogen receptors have found long-standing utility in the treatment of a variety of medical indications and in regimes for contraceptive purposes. Despite the long history of the field there still is a need for more effective, safer and more economical compounds than the existing ones. This need is the more pressing in view of advancement in health care in other areas, which has led to an increasingly longer life span. This is in particular a problem for women for whom the decline in estrogenic hormones at menopause is drastic and has negative consequences for bone strength and cardiovascular functions. For the control or prevention of estrogen sensitive tumor growth, compounds are needed which are antagonists, partial antagonists or tissue selective agonists for estrogen receptors.

The discovery of subtypes of estrogen receptors, there being an α-subtype (ERα) and a β-subtype (ERβ) of such receptors (Mosselman et al., *FEBS Letters* vol. 392 (1996) pp. 49-53 as well as EP-A-0 798 378), offers the possibility to influence one particular subtype of those two receptors more selectively, immanently resulting in more effective treatments or treatments with less side effects. Since these receptors have a different distribution in human tissue, the finding of compounds which possess a selective affinity for either of the two is an important technical progress, making it possible to provide a more selective treatment in estrogen-receptor related medical treatments, such as those for contraception and for treatment of menopausal complaints, osteoporosis, and estrogen dependent tumour control, with a lower burden of estrogen-related side-effects.

In WO 01/72713 certain compounds with an unsaturated or partially unsaturated four-ring skeleton with hydroxyl substitutions at specific locations, i.e. 2,8-dihydroxy-11H-benzo[b]fluorene and 3,9-dihydroxy-5,6-dihydro-benz[a]anthracene are disclosed. Some aryl substituted derivatives of these compounds possess high antagonism for ERβ and may also show ERα antagonism or ERα agonism as is published in the non-prepublished patent application WO 02/16316. In the latter document compounds are defined having the formula

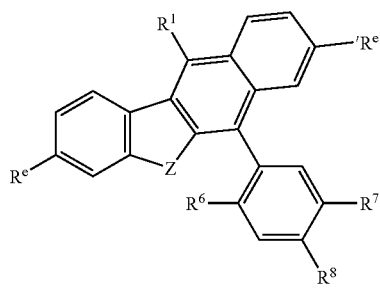

wherein:
$R^e$ and $'R^e$ are OH, optionally independently etherified or esterified;
Y is —CH$_2$— or —CH$_2$CH$_2$—;
$R^1$ is H, halogen, CF$_3$, or (1C-4C)alkyl;
$R^6$, $R^7$ and $R^8$ are independently H, halogen, —CF$_3$, —OCF$_3$, (1C-8C)alkyl, hydroxy, (1C-8C)alkyloxy, aryloxy, aryl(1C-8C)alkyl, halo(1C-8C)alkyl, —O(CH$_2$)$_m$X, wherein X is halogen or phenyl and m=2-4; —O(CH$_2$)$_m$NR$_c$R$_d$, —S(CH$_2$)$_m$NR$_c$R$_d$ or —(CH$_2$)$_m$NR$_c$R$_d$, wherein m=2-4 and wherein R$_c$, R$_d$ are independently (1C-8C)alkyl, (2C-8C)alkenyl, (2C-8C)alkynyl, or aryl, optionally substituted with halogen, —CF$_3$, —OCF$_3$, —CN, —NO$_2$, —OH, (1C-8C)alkoxy, aryloxy, carboxyl, (1C-8C)alkylthio, carboxylate, (1C-8C)alkyl, aryl, aryl(1C-8C)alkyl, halo(1C-8C)alkyl or R$_c$ and R$_d$ form a 3-8 membered ring structure, optionally substituted with halogen, —CF$_3$, —OCF$_3$, —CN, —NO$_2$, hydroxy, hydroxy(1C-4C)alkyl, (1C-8C)alkoxy, aryloxy, (1C-8C)alkylthio, carboxyl, carboxylate, (1C-8C)alkyl, aryl, aryl(1C-8C)alkyl, halo(1C-8C)alkyl.

This invention makes a compound available having the formula 1,

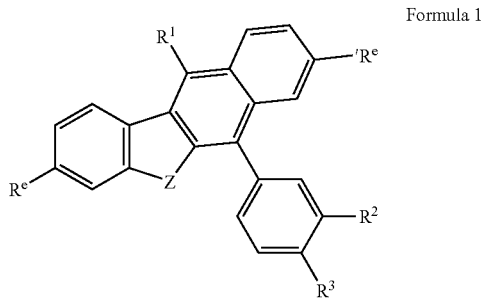

Formula 1 wherein:
$R^e$ and $'R^e$ are OH, optionally independently etherified or esterified;
Z is —CH$_2$CH$_2$— or —C(R$^4$,R$^5$)—, wherein R$^4$ and R$^5$ are independently H, (1C-2C)alkyl or form together a spiro(3C-5C)cycloalkyl;
$R^1$ is H, halogen, CF$_3$, or (1C-4C)alkyl;
$R^2$ and $R^3$ are independently H, halogen, —CF$_3$, —OCF$_3$, (1C-8C)alkyl, hydroxy, (1C-8C)alkyloxy, aryloxy, aryl (1C-8C)alkyl, halo(1C-8C)alkyl, —O(CH$_2$)$_m$X, wherein X is halogen or phenyl and m=2-4; —O(CH$_2$)$_m$NR$_a$R$_b$, —S(CH$_2$)$_m$NR$_a$R$_b$ or —(CH$_2$)$_m$NR$_a$R$_b$, wherein m=2-4 and wherein R$_a$, R$_b$ are independently (1C-8C)alkyl, (2C-8C)alkenyl, (2C-8C)alkynyl, or aryl, which alkyl, alkenyl and aryl can optionally be substituted with halogen, —CF$_3$, —OCF$_3$, —CN, —NO$_2$, —OH, (1C-8C)alkoxy, aryloxy, carboxyl, (1C-8C)alkylthio, carboxylate, (1C-8C)alkyl, aryl, aryl(1C-8C)alkyl or halo(1C-8C)alkyl; or R$_a$ and R$_b$ form a 3-8 membered ring structure, optionally substituted with halogen, —CF$_3$, —OCF$_3$, —CN, —NO$_2$, hydroxy, hydroxy(1C-4C)alkyl, (1C-8C)alkoxy, aryloxy, (1C-8C)alkylthio, carboxyl, carboxylate, (1C-8C)alkyl, aryl, aryl(1C-8C)alkyl, halo(1C-8C)alkyl.

It is thus found, as one embodiment of this invention, compounds having the formula 2

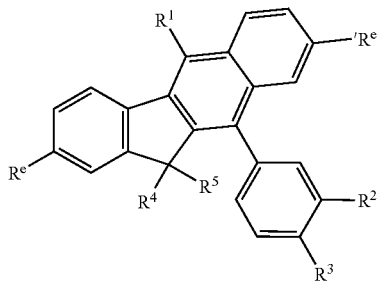

Formula 2 wherein:
$R^e$ and $'R^e$ are OH, optionally independently etherifed or esterified;
$R^1$ is H, halogen, $CF_3$, or (1C-4C)alkyl;
$R^2$ and $R^3$ are independently H, halogen, —$CF_3$, —$OCF_3$, (1C-8C)alkyl, hydroxy, (1C-8C)alkyloxy, aryloxy, aryl (1C-8C)alkyl, halo(1C-8C)alkyl, —O(CH$_2$)$_m$X, wherein X is halogen or phenyl and m=2-4; —O(CH$_2$)$_m$NR$_a$R$_b$, —S(CH$_2$)$_m$NR$_a$R$_b$ or —(CH$_2$)$_m$NR$_a$R$_b$, wherein m=2-4 and wherein R$_a$, R$_b$ are independently (1C-8C)alkyl, (2C-8C)alkenyl, (2C-8C)alkynyl, or aryl, which alkyl, alkenyl and aryl can optionally be substituted with halogen, —CF$_3$, —OCF$_3$, —CN, —NO$_2$, —OH, (1C-8C)alkoxy, aryloxy, carboxyl, (1C-8C)alkylthio, carboxylate, (1C-8C)alkyl, aryl, aryl(1C-8C)alkyl or halo(1C-8C)alkyl; or R$_a$ and R$_b$ form a 3-8 membered ring structure, optionally substituted with halogen, CF$_3$, —OCF$_3$, —CN, —NO$_2$, hydroxy, hydroxy(1C-4C)alkyl, (1C-8C)alkoxy, aryloxy, (1C-8C)alkylthio, carboxyl, carboxylate, (1C-8C)alkyl, aryl, axyl(1C-8C)alkyl, halo(1C-8C)alkyl;
$R^4$ and $R^5$ are independently (1C-2C)alkyl or form together a spiro(3C-5C)cycloalkyl.

These compounds, possessing high selective antagonism for ERβ, can in addition, have improved resistance to oxidative attack by having alkyl substitution at position 11 of the 11H-benzo[b]fluorene skeleton.

The present invention further makes the following group of very useful compounds available, that is a compound having the formula 3

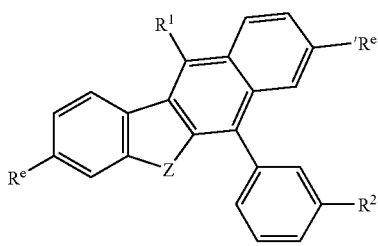

Formula 3 wherein:
$R^e$ and $'R^e$ are OH, optionally independently etherified or esterified;
Z is —CH$_2$CH$_2$— or —C(R$^3$,R$^4$)—, wherein R$^3$ and R$^4$ are independently H, (1C-2C)alkyl or form together a spiro(3C-5C)cycloalkyl;
$R^1$ is H, halogen, CF$_3$, or (1C-4C)alkyl;
$R^2$ is —O(CH$_2$)$_m$NR$_a$R$_b$, —S(CH$_2$)$_m$NR$_a$R$_b$ or —(CH$_2$)$_m$NR$_a$R$_b$, wherein m=2-4 and wherein R$_a$, R$_b$ are independently (1C-8C)alkyl, (2C-8C)alkenyl, (2C-8C)alkynyl, or aryl, which alkyl, alkenyl and aryl can be optionally substituted with halogen, —CF$_3$, —OCF$_3$, —CN, —NO$_2$, —OH, (1C-8C)alkoxy, aryloxy, carboxyl, (1C-8C)alkylthio, carboxylate, (1C-8C)alkyl, aryl, aryl(1C-8C)alkyl or halo(1C-8C)alkyl; or R$_a$ and R$_b$ form a 3-8 membered ring structure, optionally substituted with halogen, —CF$_3$, —OCF$_3$, —CN, —NO$_2$, hydroxy, hydroxy(1C-4C)alkyl, (1C-8C) alkoxy, aryloxy, (1C-8C)alkylthio, carboxyl, carboxylate, (1C-8C)alkyl, aryl, aryl(1C-8C)alkyl, halo(1C-8C)alkyl.

More specific embodiments of the previously defined embodiments can be obtained by selecting H, halogen or CF$_3$ for $R^1$. Compounds according to the formulas whereby $R^1$ is halogen, whereby chlorine is most preferred, are particularly potent and selective for the ERβ.

Another embodiment of the invention is a non-steroidal compound with a 10-Aryl-11H-benzo[b]fluorene skeleton having the formula 4

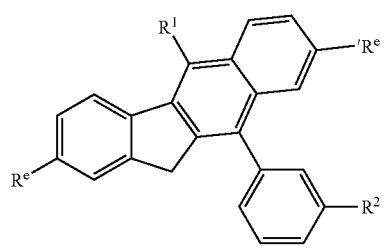

Formula 4 wherein:
$R^e$ and $'R^e$ are OH, optionally independently etherified or esterified;
$R^1$ is H, halogen or CF$_3$;
$R^2$ is —O(CH$_2$)$_m$NR$_a$R$_b$, —S(CH$_2$)$_m$NR$_a$R$_b$ or —(CH$_2$)$_m$NR$_a$R$_b$, wherein m=2-4 and wherein R$_a$, R$_b$ are independently (1C-8C)alkyl, (2C-8C)alkenyl, (2C-8C) alkynyl, or aryl, which alkyl, alkenyl and aryl can be optionally substituted with halogen, —CF$_3$, —OCF$_3$, —CN, —NO$_2$, —OH, (1C-8C)alkoxy, aryloxy, carboxyl, (1C-8C)alkylthio, carboxylate, (1C-8C)alkyl, aryl, aryl(1C-8C)alkyl or halo(1C-8C)alkyl; or R$_a$ and R$_b$ form a 3-8 membered ring structure, optionally substituted with halogen, —CF$_3$, —OCF$_3$, —CN, —NO$_2$, hydroxy, hydroxy(1C-4C)alkyl, (1C-8C) alkoxy, aryloxy, (1C-8C)alkylthio, carboxyl, carboxylate, (1C-8C)alkyl, aryl, aryl(1C-8C)alkyl, halo(1C-8C)alkyl.

For compounds having formula 4 it is preferred to select those in which
$R^2$ is —O(CH$_2$)$_m$NR$_a$R$_b$, wherein m=2-3 and R$_a$, R$_b$ are independently (1C-5C)alkyl, (3C-5C)alkenyl, or aryl, which alkyl, alkenyl and aryl can be optionally substituted with OH or methoxy, or R$_a$ and R$_b$ form a 4-7 membered ring structure selected from the list: azetidine, pyrrolidine, 3-pyrroline, piperidine, piperazine, tetrahydropyridine, morpholine, thiomorpholine, thiazolidine, homopiperdine, tetrahydroquinoline and 6-azabicyclo[3.2.1]octane, which 4-7 membered ring structure can optionally be substituted with OH, methoxy, acetyl, carboxylate, (1C-3C)alkyl, phenyl, benzyl, and phenylethyl.

In those cases that a compound of the invention contains a basic amine function, the compound may be used as a free base or as a pharmaceutically acceptable salt such as hydrochloride, acetate, oxalate, tartrate, citrate, phosphate, maleate or fumarate.

The ester and ether compounds in the collection of compounds according to the invention often have activity as prodrug. A prodrug is defined as being a compound which converts in the body of a recipient to a compound as defined by the formulas 1 to 4 and to the free hydroxyl compounds of the above defined compounds. Preferred ester and ether prodrugs are carboxylic acid esters or alkyl ethers on one or both hydroxyl groups, and more preferred prodrugs are (2C-6C)carboxylic acid esters, such as esters of (iso)butanoic acid, or (1C-4C) alkyl ethers. In general, the hydroxy groups can for example be substituted by allyl*oxy, alkenyl*oxy, acyl*oxy, aroyloxy, alk*oxycarbonyloxy, sulfonyl groups or phosphate groups, whereby the carbon chain length of the groups denoted with an asterisk (*) is not considered to be sharply delimited, while aroyl generally will comprise a phenyl, pyridinyl or pyrimidyl, which groups can have substitutions customary in the art, such as alkyl*oxy, hydroxy, halogen, nitro, cyano, and (mono-, or dialkyl*-)amino. The length of the alkyl, alkenyl and acyl groups is selected depending on the desired properties of the prodrugs, whereby the longer chained prodrugs with for example lauryl or caproyl chains are more suitable for sustained release and depot preparations. It is known that such substituents spontaneously hydrolyse or are enzymatically hydrolysed to the free hydroxyl substituents on the skeleton of the compound. Such prodrugs will have biological activity comparable to the compounds to which they are converted in the body of the recipients. The active compound to which a prodrug is converted is called the parent compound. The onset of action and duration of action as well as the distribution in the body of a prodrug may differ from such properties of the parent compound.

Other terms used in this description have the following meaning:
alkyl is a branched or unbranched alkyl group, for example methyl, ethyl, propyl, isopropyl, butyl, sec-butyl, tert-butyl, hexyl, octyl, capryl, or lauryl;
alkenyl is a branched or unbranched alkenyl group, such as ethenyl, 2-butenyl, etc.;
alkynyl is a branched or unbranched alkynyl group, such as ethynyl and propynyl;
halogen refers to fluorine, chlorine, bromine and iodine;
aryl is a mono- or polycyclic, homo- or heterocyclic aromatic ring system, such as phenyl, naphtyl or pyridinyl; a monocyclic ring with 6 atoms is preferred for use;
a ring system or structure is referring to a chemical group in which all atoms are involved in formed rings, which rings can be saturated or (partially) unsaturated and comprise C, O, S or N atoms;
aroyl is arylcarbonyl such as a benzoyl group;
alkanoyl means a formyl or alkylcarbonyl group such as formyl, acetyl and propanoyl;
acyl is a (substituent-)carbonyl group, such as an aroyl or alkanoyl;
carboxyl is a —COOH substituent, making the compound an organic acid;
carboxylate is an ester or salt of a carboxyl substituent;
3-8 membered ring structure refers to a single ring or two or more fused rings comprising 3-8 atoms, for example, when a nitrogen atom is in the ring, an azetidine, pyrrolidine, 3-pyrroline, piperidine, piperazine, tetrahydropyridine, morpholine, thiomorpholine, thiazolidine, homopiperidine, tetrahydroquinoline or 6-azabicyclo [3.2.1]octane.

The prefixes (1C-4C), (2C-4C) etc. have the usual meaning to restrict the meaning of the indicated group to those with 1 to 4, 2 to 4 etc. carbon atoms.

The estrogen-receptor affinity profile of the compounds according to the present invention, makes them suitable for use in estrogen-receptor related medical treatments, in the sense that these compounds are improved selective anti-estrogens, partial anti-estrogen or partial estrogens. Estrogen-receptor related medical treatments specifically named are those for contraception or for treatment or prevention of benign prostate hypertrophy, cardiovascular disorders, menopausal complaints, osteoporosis, estrogen dependent tumour control or central nervous system disorders such as depression or Alzheimer's disease. In particular the most selective compounds for the ERβ receptor are suitable for estrogen-receptor related medical treatments under diminished estrogen-related side-effects. This is most desirable when these compounds are used in the treatment of osteoporosis, cardiovascular disorders and central nervous system disorders such as depression or Alzheimer's disease. Selective blockade of ERβ-receptors with compounds of this invention can be used to prevent and reduce malignant tumor growth and hyperplasias. The receptor selectivity helps to effectuate tissue selectivity. Those tissues rich in ERβ-receptors can be protected by ERβ-receptor antagonists from the risk of stimulation of growth by estrogenic agonists. The latter can be of endogenous origin or from exogenous origine when administered during estrogenic treatment, for example for hormone replacement after menopause. Tissues that can benefit from protection in view of the presence of ERβ-receptors are prostate, testes (human), lung, colon and endometrium. In particular, endometrium proliferation can be reduced by ERβ antagonists of the invention.

The compounds can be produced by various methods known in the art of organic chemistry in general. More specifically the routes of synthesis as illustrated in the schemes and examples can be used.

Scheme 1

A general procedure that can be used to prepare the compounds.

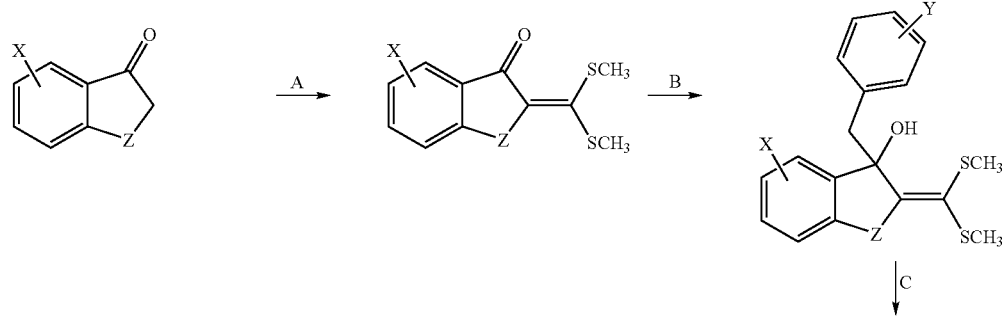

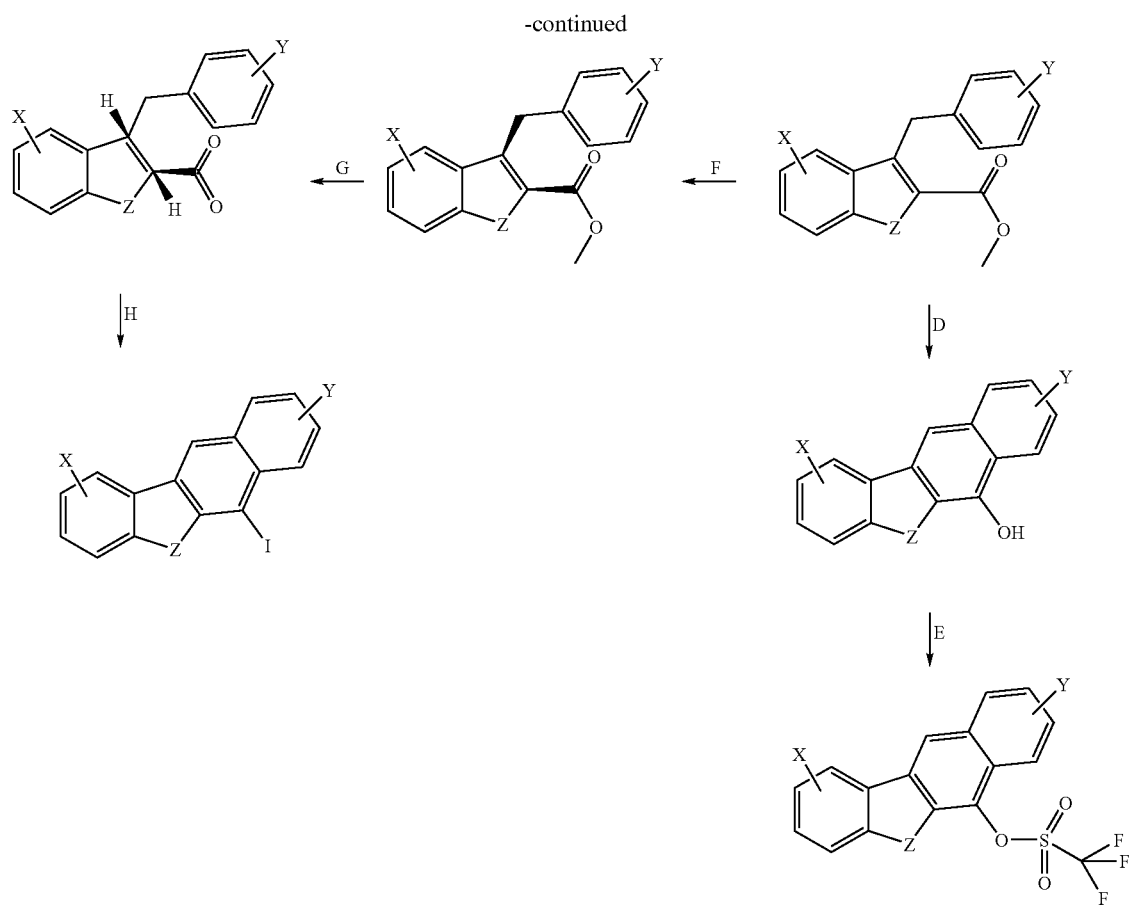

Z = CH₂ or CH₂CH₂
X, Y = OCH₃, occasionally accompannied by other substituents

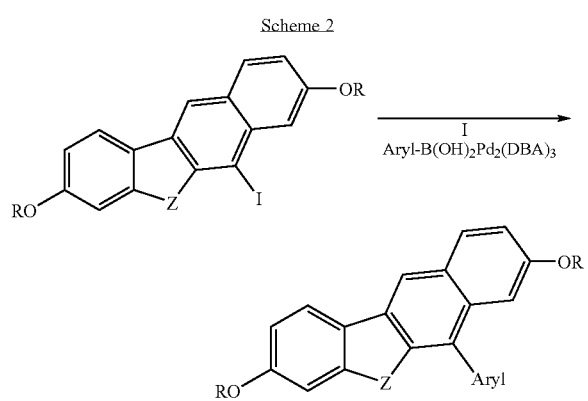

Scheme 2

R is protecting group

With reference to scheme 1, the benzofluorene (Z=CH₂) and the benzanthracene (Z=CH₂CH₂) skeleton can be assembled in an identical manner. In step A adequately substituted indanones or tetralones are treated with CS₂ under appropriate basic conditions to introduce a dithioketene function (in fact serving as a carboxylate equivalent), after which procedure reaction with an organo-metallic derivative of a substituted benzylhalide (preferably a Grignard derivative) in step B, followed by alcoholysis (step C) leads to an α,β-unsaturated ester. At this stage an acid catalyzed cyclization (step D) immediately leads to the phenolic benzofluorene (or benzanthracene). Conversion of this into a reactive intermediate (like triflate) in step E allows the introduction of the desired functionalities (like aryl groups, carboxylates etc) by means of known organometallic techniques.

If the mentioned α,β-unsaturated ester is first hydrogenated in step F prior to cyclization (step G), the indicated ketones become available. They may be easily converted into the aromatic iodide in step H. These, under circumstances may be more reactive than the afore-mentioned triflates and provide valuable alternatives for functionalization (step I in scheme 2).

Alkylation on the 11 [H] position can be performed in two separate steps, using appropriate bases to generate anions at the methylene position of the 11[H]benzofluorene skeleton followed by treatment with alkylating agents. Deprotection of the silyl protecting group, followed by standard functional group transformations provides the desired amines.

Ester prodrugs can be made by esterification of compounds with free hydroxyl groups by reaction with appropriate acyl chlorides in pyridine. Free dihydroxy compounds having formula 1 can be made by hydrolysis of ether precursors.

The present invention also relates to a pharmaceutical composition comprising the non-steroidal compound according to the invention mixed with a pharmaceutically acceptable auxliary, such as described in the standard reference Gennaro et al, *Remmington: The Science and Practice of Pharmacy*, (20th ed., Lippincott Williams & Wilkins, 2000, see especially Part 5: Pharmaceutical Manufacturing). Suitable auxiliaries are made available in e.g. the Handbook of Pharmaceutical Excipients ($2^{nd}$ Edition, Editors A. Wade and P. J. Weller; American Pharmaceutical Association; Washington; The Pharmaceutical Press; London, 1994). The mixture of the compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the compounds for the manufacture of a medicine for an estrogen receptor related treatment, characterised in that the treatment is to antagonise the ERβ. In the context of the present use the antagonism does not have to be complete, but also includes partial antagonism.

Furthermore, the invention relates to the use of the non-steroidal compound according to the invention for the manufacture of a medicament for estrogen-receptor related treatments and treatment of estrogen-receptor related disorders such as peri- and/or post-menopausal complaints. Thus the invention also pertains to the medical indications of peri- and/or post-menopausal (climacteric) complaints and osteoporosis, i.e. a method of treatment in the field of hormone replacement therapy (HRT), comprising the administration to a patient, being a woman, of a compound as described hereinbefore (in a suitable pharmaceutical dosage form).

Further, the invention relates to the use of the non-steroidal compound according to the invention in the manufacture of a medicament having contraceptive activity. Thus the invention also pertains to the medical indication of contraception, i.e. a method of contraception comprising the administration to a subject, being a woman or a female animal, of a progestogen and an estrogen as is customary in the field, wherein the estrogen is a compound as described hereinbefore (in a suitable pharmaceutical dosage form).

Finally the invention relates to the use of the non-steroidal compound for the manufacture of a medicament having selective estrogenic and/or anti-estrogenic activity, such a medicament being generally suitable in the area of HRT (hormone replacement therapy).

The dosage amounts of the present compounds will be of the normal order for estrogenic compounds, e.g. of the order of 0.01 to 100 mg per administration.

The invention is further illustrated hereinafter with reference to some unlimitative examples and the corresponding formula schemes referred to. Compounds are identified by numbers (in bold letter type) with reference to the corresponding numbers in the schemes. Abbreviations used in the schemes: Me is methyl, Bn is benzyl, ph is phenyl, aryl represents the substituted phenyl as in formula 1.

EXAMPLES

Example 1

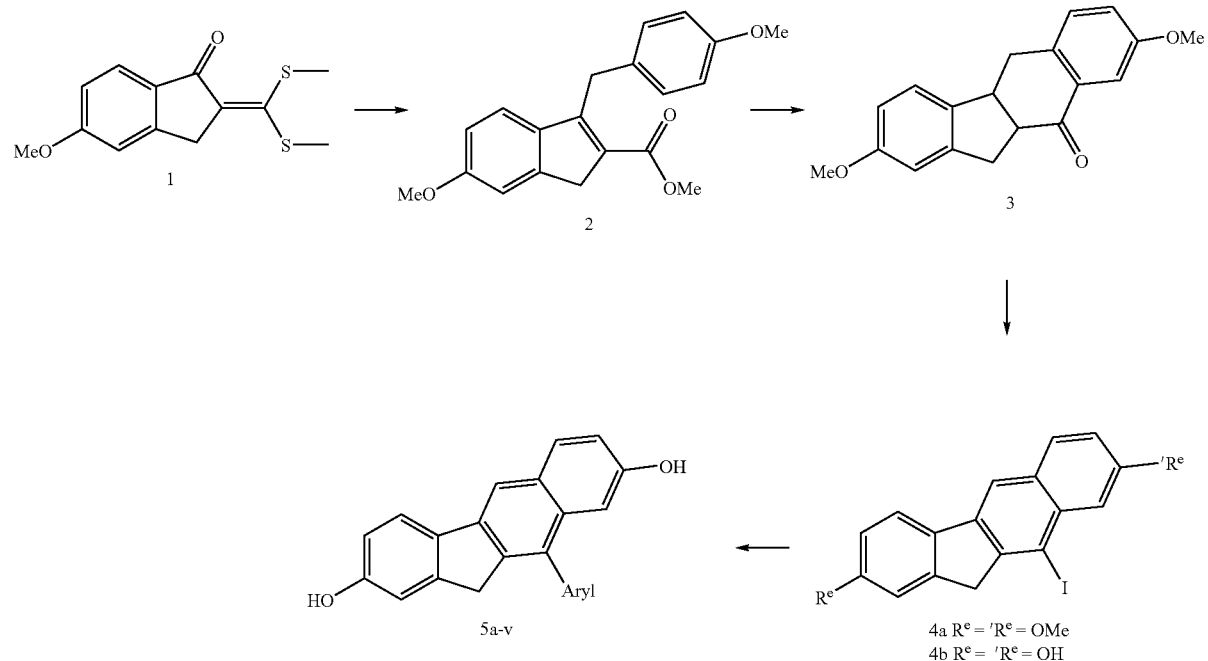

Preparation of Precursor 10-iodo-2,8-dihydroxy-11H-benzo[b]fluorene (4b).

59 ml 4-methoxybenzyl-magnesium chloride (0.2 M in diethyl ether) was added to 1 [J. V. Ram and M. Nath, *Indian J. Chem. Sect. B*; 34, 416-422 (1995)] (11.6 mmol) in 70 ml THF at 0° C. and the reaction mixture was stirred for 0.5 hour at 20° C. The mixture was poured into saturated aq. NH$_4$Cl, extracted with diethyl ether and dried over MgSO$_4$. After evaporation of the solvent the crude product was purified by chromatography on silica gel (heptane/ethyl acetate). The pure fractions were concentrated and the material obtained was taken up in 95 ml methanol and treated with BF$_3$.Et$_2$O (28 mmol). After 0.5 hour the temperature was raised to 65° C. and after 0.5 hour the reaction mixture was poured into water, extracted with CH$_2$Cl$_2$ and the organic layer washed with NaHCO$_3$ (aq). The extract was dried over MgSO$_4$, concentrated and the residue was recrystallised from methanol to afford pure 2 in 45% yield (Rf=0.48 heptane/ethyl acetate (3:2)).

A mixture of 2 (5 mmol) and palladium on carbon (10% Pd (w/w), 300 mg) in 120 ml ethanol/acetic acid (5:1) was stirred under an atmosphere of hydrogen for 1 hour. The catalyst was removed by filtration and the filtrate was concentrated.

The residue was dissolved in methanesulfonic acid and stirred at 90° C. for 15 minutes after which the mixture was poured into ice water and extracted with ethyl acetate. The organic layer was washed with NaHCO$_3$(aq) and dried over MgSO$_4$. Chromatography on silica gel (heptane/ethyl acetate) gave pure 3 in 85% yield. (Rf=0.49 heptane/ethyl acetate (2:1)); MP 96-98° C.

The compound 3 (0.34 mmol) was dissolved in ethanol and 1 ml hydrazine monohydrate was added. After 4 hours refluxing, water was added and the hydrazone was extracted with CH$_2$Cl$_2$. The organic layer was washed with water, dried and concentrated. The residue was taken up in 1.5 ml triethylamine and 0.2 g iodine in 0.7 ml THF was added at 0° C. After 1 hour the reaction mixture was diluted with toluene, poured into ice water and extracted with toluene. The organic layer was washed with 1N HCl and saturated NaHCO$_3$(aq), dried over MgSO$_4$ and concentrated. The residue was dissolved in 8 ml m-xylene/toluene (2:1) palladium on carbon (10% w/w, 100 mg) was added and the mixture was heated at 125° C. for 2 hours. After cooling the catalyst was filtered off, the filtrate was concentrated and the residue was purified on silica gel (heptane/ethyl acetate). The appropriate fractions were collected and concentrated to give pure 4a. Compound 4a was dissolved in 30 mL CH$_2$Cl$_2$ and treated with BBr$_3$ (3.5 mmol). After 1 hour another 2.1 mmol of BBr$_3$ was added. After 1.5 hours the mixture was carefully poured into sat. NaHCO$_3$ (aq) and extracted with ethyl acetate. The organic layer was dried over MgSO$_4$ and concentrated. Chromatography on silica gel (toluene/ethyl acetate) afforded pure 4b in 62% yield. (Rf=0.50 toluene/ethyl acetate (4:1)); ESI-MS: M+H=375.2, M−H=373.0.

General Procedure to Prepare Compounds 5a-v (10-aryl-2,8-dihydroxy-11H-benzo[b]fluorenes)

(Reference to Scheme 3)

A mixture of 10-iodo-benzofluorene derivative 4 (27 μmol), 3 mg Pd$_2$(dba)$_3$, 0.2 M Na$_2$CO$_3$(aq), 30 μmol arylboronic acid and 1 ml 2-methoxy-ethanol was heated for 5 hours at 55° C. Ethyl acetate and water were added to the reaction mixture and the organic layer was separated, dried over MgSO$_4$ and concentrated. The residue was purified on silica gel (toluene/ethylacetate) to give pure 5a-v (yields 14-52%).

| Compound | ARYL | Yield (%) | [M − H] |
|---|---|---|---|
| 5a | 4-chlorophenyl | 37 | [M − H] = 357.2 |
| 5b | 2-naphthyl | 44 | [M − H] = 373.2 |
| 5c | 3-methoxyphenyl | 32 | [M − H] = 353.4 |
| 5d | 3-trifluoromethylphenyl | 54 | [M − H] = 391.3 |
| 5e | 4-methylphenyl | 42 | [M − H] = 337.4 |
| 5f | 3-chloro-4-fluorophenyl | 40 | [M − H] = 375.2 |
| 5g | 3,4-methylenedioxophenyl | 49 | [M − H] = 367.4 |
| 5h | 4-phenylphenyl | 55 | [M − H] = 399.4 |
| 5i | 2-benzothiazole | 30 | [M − H] = 379.4 |
| 5j | 3-fluorophenyl | 27 | [M − H] = 341.4 |
| 5k | 4-methoxyphenyl | 27 | [M − H] = 353.4 |
| 5l | 4-fluorophenyl | 52 | [M − H] = 341.4 |
| 5m | 3,4-dichlorophenyl | 14 | [M − H] = 390.8 |
| 5n | 3-chlorophenyl | 37 | [M − H] = 357.0 |
| 5o | 4-trifluoromethylphenyl | 22 | [M − H] = 391.4 |
| 5p | 3-methylphenyl | 21 | [M − H] = 337.2 |
| 5q | 3-isopropylphenyl | 40 | [M − H] = 365.0 |
| 5r | 4-trifluoromethyloxyphenyl | 41 | [M − H] = 407.2 |
| 5s | 3-fluoro-4-phenylphenyl | 22 | [M − H] = 417.0 |
| 5t | 4-methylthiophenyl | 32 | [M − H] = 371.2 |
| 5u | 2-trifluoromethylphenyl | 20 | [M − H] = 391.0 |
| 5v | Phenyl | 25 | [M − H] = 323.2 |

Example 2

Scheme 4

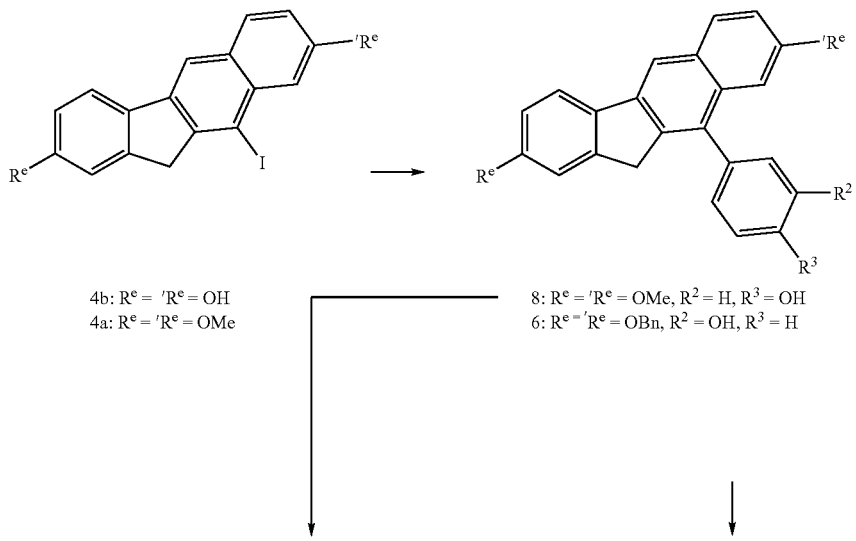

4b: R$^e$ = 'R$^e$ = OH
4a: R$^e$ = 'R$^e$ = OMe

8: R$^e$ = 'R$^e$ = OMe, R$^2$ = H, R$^3$ = OH
6: R$^e$ = 'R$^e$ = OBn, R$^2$ = OH, R$^3$ = H

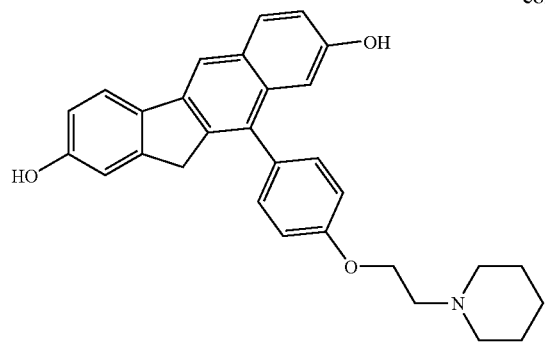

9

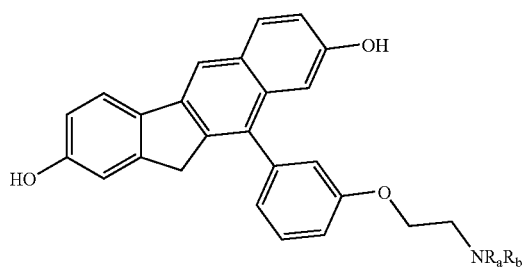

7a: $NR_aR_b$ = pyrrolidine
7b: $NR_aR_b$ = dimethylamine
7c: $NR_aR_b$ = morpholine
7d: $NR_aR_b$ = diethylamine
7e: $NR_aR_b$ = piperidine Compound 7a-d A mixture of 4b (0.94 mmol), potassium carbonate (3.0 mmol) and benzyl bromide (2.1 mmol) in acetone (10 ml) was refluxed overnight after which the mixture was poured into water and extracted with ethyl acetate. The organic layer was dried over $MgSO_4$, concentrated and purified by chromatography on silica gel (heptane/ethyl acetate).

The purified product (0.43 mmol) was taken up in 2-methoxyethanol (16 ml) and $Pd_2(dba)_3$ (36 μmol), 3-hydroxyphenylboronic acid pinacolester (0.45 mn and $Na_2CO_3$ (2M in water, 2 ml) were added. The mixture was stirred for 30 minutes at 60° C., poured into water and extracted with ethyl acetate. The organic layer was dried over $MgSO_4$, concentrated and purified by chromatography on silica gel ($CH_2Cl_2$/methanol) to give pure 6 in 56% yield=0.34 (heptane/ethyl acetate (7:3)).

A mixture of 6 (48 μmol), 1-(2-chloroethyl)pyrrolidine hydrochloride (76 μm and cesium carbonate (0.15 mmol) in acetonitrile (2 ml) was stirred for 3 hr at 50° C. The mixture was poured into water and extracted with ethyl acetal the organic extract was dried over $MgSO_4$, the solvent evaporated and the residue was purified by chromatography on silica gel ($CH_2Cl_2$/methanol). The pure fractions were concentrated and the material obtained was dissolved in ethyl acetate (3 ml). Pd/C (10% w/w, 25 mg) and 3 drops of acetic acid were added and the mixture was stirred under an atmosphere of hydrogen for 5 hours. The catalyst was removed by filtration and the filtrate was concentrated. The residue was purified by chromatography on silica gel ($CH_2Cl_2$/methanol yield pure 7a in 22% yield. Rf=0.14 ($CH_2Cl_2$/methanol (9:1)), ESI-MS: M+H 438.4, M−H=436.2.

Compound 7b

Compound 7b was prepared from 6 in 5% yield, in the same fashion as described for the preparation of 7a, using 2-dimethylaminoethyl chloride hydrochloride (Rf=0.18 $CH_2Cl_2$/methanol (9:1)); ESI-MS: M+H=412.4, M−H=410.4.

Compound 7c

Compound 7c was prepared from 6 in 32% yield, in the same fashion as described for the preparation of 7a, using 1-(2-chloroethyl)morpholine hydrochloride instead of 1-(2-chloroethyl)pyrrolidine hydrochloride (Rf=0.21 $CH_2Cl_2$/methanol (9:1)); ESI-MS: M+H=454.4, M−H=452.2.

Compound 7d

Compound 7d was prepared from 6 in 65% yield, in the same fashion as described for the preparation of 7a, using 2-diethylaminoethyl chloride hydrochloride instead of 1-(2-chloroethyl)pyrrolidine hydrochloride (Rf=0.17 $CH_2Cl_2$/methanol (9:1)); ESI-MS: M+H=440.4, M−H=438.2.

Compound 7e

Compound 7e was prepared from 6 in 18% yield, as described for the preparation of 7a, using 1-(2-chloroethyl)piperidine hydrochloride instead of 1-(2-chloroethyl)pyrrolidine hydrochloride (Rf=0.15 $CH_2Cl_2$/methanol (9:1)); ESI-MS: M+H=452.4, M−H=450.2.

Compound 9

A mixture of 4a (0.30 mmol), $Pd_2(dba)_3$ (0.40 μmol), 4-hydroxyphenylboronic acid (0.30 mmol) and sodium carbonate (2 M in water, 4 ml) in 12 ml 2-methoxyethanol was stirred at 60° C. After 30 minutes the mixture was poured into water and extracted with ethyl acetate. The organic extract was dried over $MgSO_4$, concentrated and purified by chromatography on silica gel (toluene/ethyl acetate) to give 8 in 65% yield. Rf=0.24 (toluene/ethyl acetate (8:2)).

Compound 8 (0.16 mmol) was dissolved in toluene (3 ml). Sodium hydride (0.4 mmol) and 1-(2-chloroethyl)piperidine hydrochloride (0.2 mmol) were added and the mixture was refluxed for 3.5 hours. The reaction mixture was poured into water and extracted with ethyl acetate. The organic extract was dried over $MgSO_4$, concentrated and purified by chromatography on silica gel (toluene/methanol).

The pure fractions were collected and concentrated, the material obtained (46 μmol) was dissolved in $CH_2Cl_2$ and treated with ethanethiol (0.62 mmol) and aluminum chloride (95 μmol) at RT. After 16 hours the dark red mixture was poured into water and extracted with ethyl acetate. The organic extract was dried over $MgSO_4$, concentrated and purified by chromatography on silica gel ($CH_2Cl_2$/methanol) to give 9 in 22% yield. Rf=0.23 (toluene/methanol (85:15)), ESI-MS: M+H=452.4, M−H=450.2.

Example 3

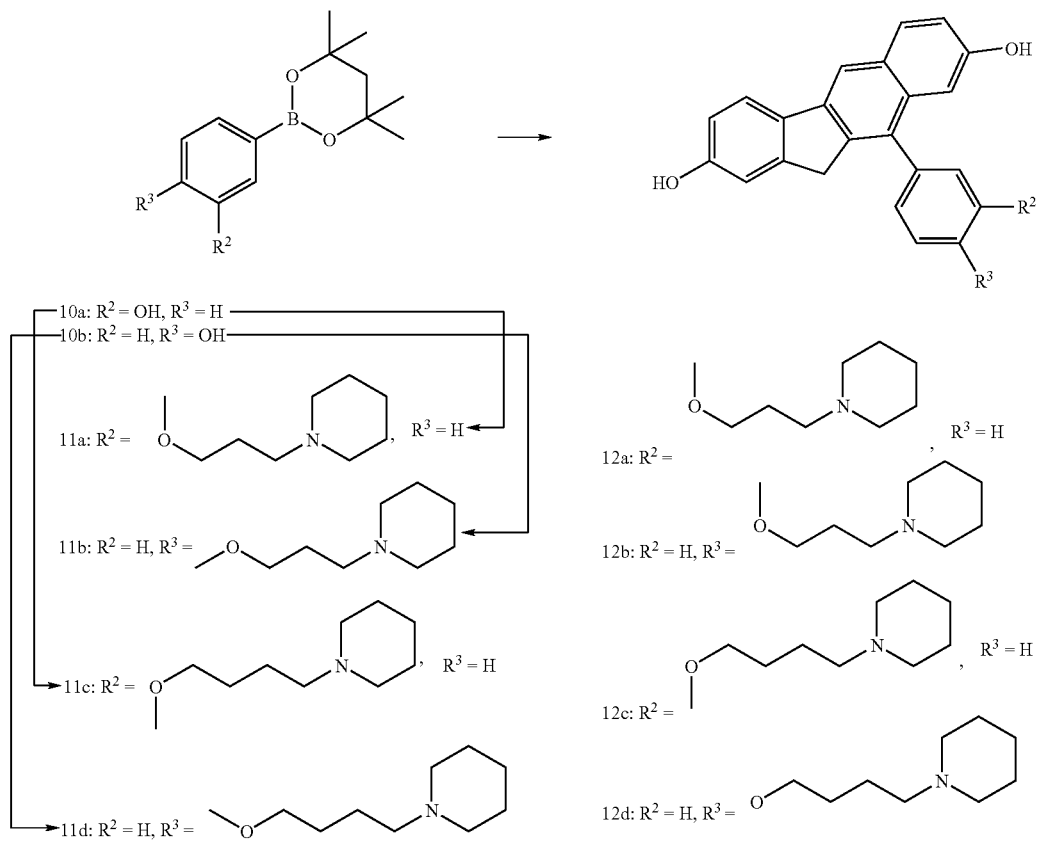

Scheme 5

Compound 12a

A mixture of 3-hydroxyphenylboronic acid pinacolester 10a (0.68 mmol), cesium carbonate (0.68 mmol) and 1-bromo-3-chloropropane (0.80 mmol) in acetonitrile (3 ml) was stirred overnight at RT. Additional cesium carbonate (0.31 mmol) and 1-bromo-3-chloropropane (0.4 mmol) were added and the mixture was stirred overnight at 60° C. The mixture was poured into water and extracted with $CH_2Cl_2$. The $CH_2Cl_2$-layer was dried over $MgSO_4$, concentrated and purified by chromatography on silica gel (toluene/ethyl acetate). The purified product was dissolved in piperidine and stirred for 48 hours at 45° C. The solid material (piperidine.HCl) was filtered off and the filtrate was concentrated to give 11a in 88% yield. Rf=0.05 (toluene/ethyl acetate (4:1)).

A mixture of 4b (67 μmol), 11a (86 μmol), $PdCl_2(dppf_2$ (5 μmol) and sodium carbonate (2 M in water, 0.25 ml) in 2.5 ml 2-methoxyethanol was stirred at 90° C. After 2 hours the mixture was poured into water and extracted with ethyl acetate. The organic extract was dried over $MgSO_4$, concentrated and purified by chromatography on silica gel ($CH_2Cl_2$/methanol). The appropriate fractions were collected and concentrated, the material obtained was recrystallised from $CHCl_3$ to give 12a in 38% yield. Rf=0.42 ($CH_2Cl_2$/methanol (85:15)).

Compound 12b

A mixture of 4-hydroxyphenylboronic acid pinacolester 10b (0.68 mmol), potassium hydroxide (2.1 mmol) and 1-bromo-3-chloropropane (2.8 mmol) in methanol (2 ml) was refluxed for 24 hours. The mixture was poured into water and extracted with ethyl acetate. The organic extract was dried over $MgSO_4$, concentrated and purified by chromatography on silica gel (toluene/ethyl acetate). The purified product was dissolved in piperidine and stirred overnight at 50° C. The solid material (piperidine.HCl) was filtered off and the filtrate was concentrated to give 11b in 80% yield. Rf=0.10 (toluene/methanol (9:1)).

Compound 12b was prepared from 4a and 11b in 20% yield, in a similar fashion as described for the preparation of 12a. Rf=0.42 ($CH_2Cl_2$/methanol (85:15)), ESI-MS: M+H=466.4, M−H=464.6

Compound 12c

Compound 12c was prepared from 10a in 25% yield, as described for the preparation of 12a, using 1-bromo-4-chloro-butane instead of 1-bromo-3-chloro-propane. Rf=0.21 ($CH_2Cl_2$/methanol (8:2)), ESI-MS: M+H=480.6, M−H=478.2

Compound 12d

To mixture of 1,4-diiodobutane (5 mmol) and cesium carbonate (0.68 mmol) in acetonitrile (2 ml) was portion-wise added 4-hydroxyphenylboronic acid pinacolester 10b (0.68 mmol) at 40° C. After 2.5 hours water was added and the mixture was extracted with ethyl acetate. The organic layer was dried over $MgSO_4$, concentrated and purified by chromatography on silica gel (heptane/toluene). The purified product was dissolved in piperidine and stirred at RT for 2 hours. The solid material (piperidine.HI) was filtered off and the filtrate was concentrated to give 11d in 32% yield. Rf=0.55 (toluene/methanol (8:2)).

Compound 12d was prepared from 4b and 11d in 13% yield, in a similar fashion as described for the preparation of 12a. Rf=0.22 (CH$_2$Cl$_2$/methanol (8:2)), ESI-MS : M+H 480.4, M−H=478.2

Example 4 stirred at room temperature for 16 hours. The reaction mixture was taken up in ethyl acetate, washed with water and saturated NaHCO$_3$ solution, dried over MgSO$_4$ and concentrated. The crude product was purified by chromatography on silica gel (CH$_2$Cl$_2$/methanol) to give pure 15a in 93% yield. Rf=0.47 (CH$_2$Cl$_2$/methanol (9:1))

Compound 15b

22 μM of bromide 14 was refluxed for 1.5 hours with 100 μM LiAlH$_4$ in THF. Water and ethyl acetate were added to

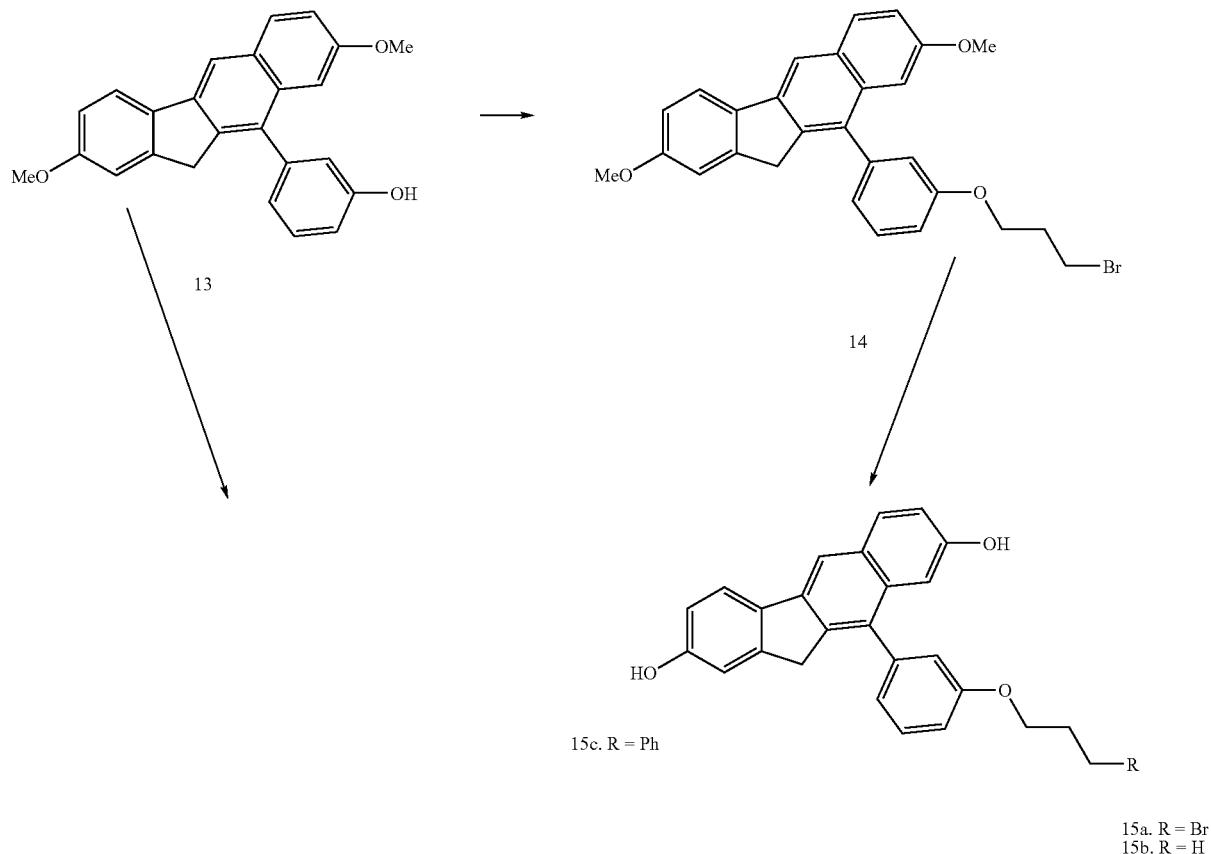

Scheme 6

Compound 14

A mixture of 2.03 mmole of 1,3-dibromopropane and 1.02 mmole of potassium carbonate in 10 ml of acetone was warmed to 40° C. To this solution 0.51 mmole of 13 in 10 ml of acetone was added dropwise and the reaction mixture was stirred at 40° C. for 23 hours. An additional is mixture of 2.03 mmole of 1,3-dibromopropane and 1.02 mmole of potassiumcarbonate in 5 ml of acetone was added and the reaction mixture stirred for 4 hours at reflux temperature. The reaction mixture was taken up in ethyl acetate and water, washed with water and saturated NaCl solution, dried over MgSO$_4$ and concentrated. The crude product was purified by chromatography on silica gel (heptane/ethyl acetate) to give pure 14 in 65% yield. Rf=0.64 (heptane/diethylether (7:3))

Compound 15a

82 μmole of 14 was dissolved in 6 ml of dry CH$_2$Cl$_2$. 327 μmole of BF$_3$.S(CH$_3$)$_2$ was added and the solution was the reaction mixture and the organic layer was separated, dried over MgSO$_4$ and concentrated. The residue was purified on silicagel (methylene/methanol) to give pure 3'-O-propyl compound 15b in yield 37%. Rf=0.40 (heptane-ethyl acetate 7:3).

Compound 15c

54 μM of compound 13 was reacted with 1.7 mM 1-bromo-3-phenylpropane in the presence of 1.7 mM K$_2$CO$_3$ in 3 ml acetone at room temperature. After 24 hours the salts were removed by filtration. The filtrate was concentrated and redissolved in methylene chloride. The mixture was extracted with water, dried over MgSO$_4$ and concentrated. The residue was purified by chromatography on silica gel (heptane/ethylacetate). (yield=88%).

47 μM of the resulting product was demethylated with 1.9 mM (CH$_3$)$_3$S.BF$_3$ in CH$_2$Cl$_2$ for one night. Ethyl acetate and water were added to the reaction mixture and the organic layer was separated, dried over MgSO$_4$ and concentrated.

The residue was purified on silica gel (heptane/ethylacetate) to give pure compound 15c in yield=57%. Rf 0.7 (heptane ethyl acetate 8:2)
Example 5
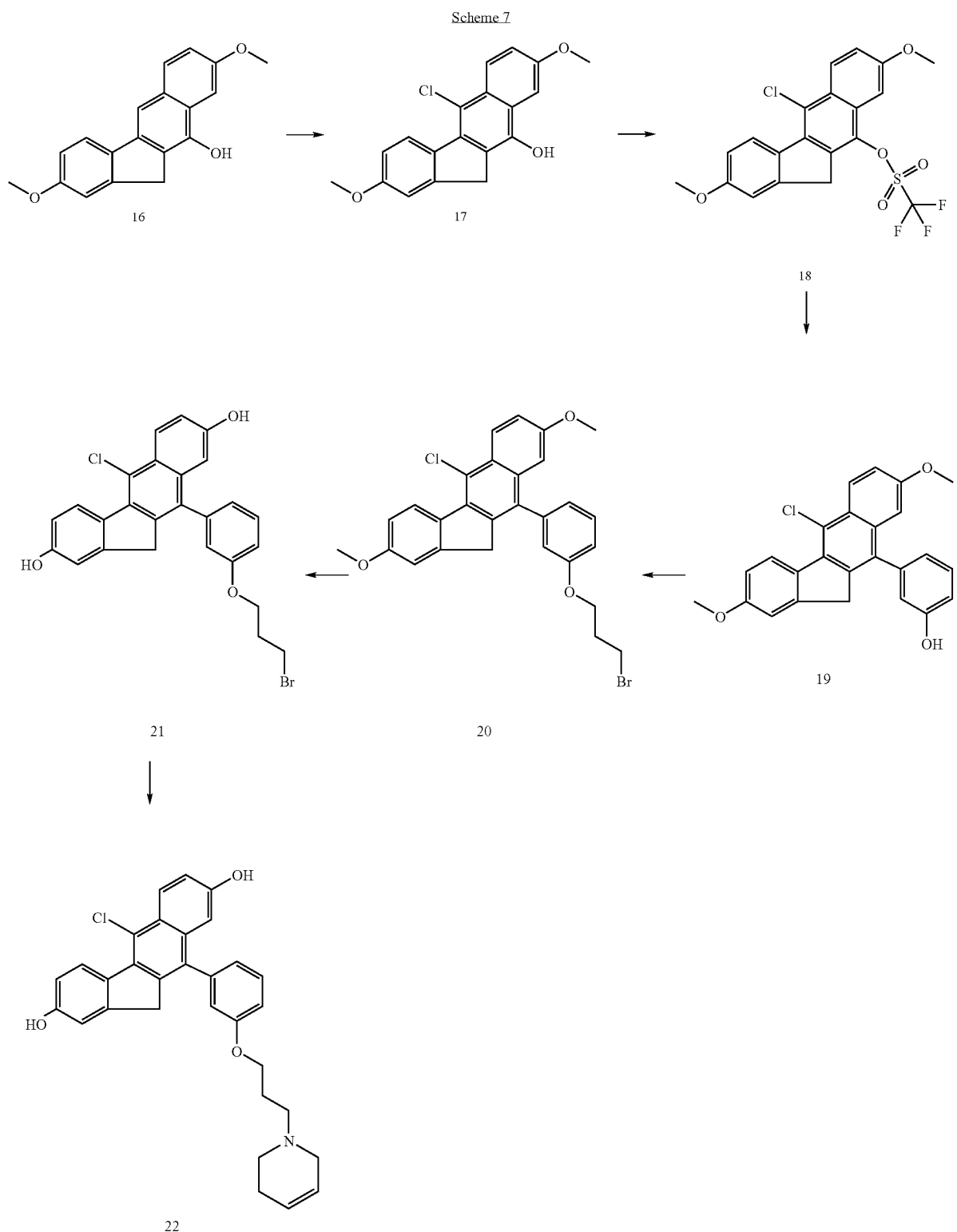

2,8-dimethoxy-10-hydroxy-11H-benzo[b]fluorene (Compound 16)

The compound 2,8-dimethoxy-10-hydroxy-11H-benzo[b]fluorene (Compound 16) 1 was prepared from its corresponding ester as explained above for step 4 in scheme 1. An amount of 3 g of the corresponding unsaturated ester was added in small portions over a few minutes to 30 ml of methanesulphonic acid at 60° C. After stirring for ½ hr the cyclization was complete. The mixture was then poured onto ice water and stirred for an additional ½ hr. The product was filtered, washed with water and thoroughly dried over $P_2O_5$, to give 2.2 gr of compound 16.

$R_f$ 0.38 (heptane/eth. ac. 7/3). NMR (DMSO) 3.82, 3.88 (2×3H, s, $OCH_3$), 3.95 (s, 2H, $CH_2$), 9.57 (s, 1H, OH), 6.97, 7.11, 7.20, 7.55, 7.51, 7.75, 7.80 (7H's, aromatic protons)

5-chloro-2,8-dimethoxy-10-hydroxy-11H-benzo[b]fluorene (Compound 17)

To a solution of 800 mg of compound 16 in 10 ml of DMF was added 850 mg of 2,2,3,4,5,6-hexachlorocyclohexa3,5-diene in small portions over 5 minutes. The mixture was stirred for 1 hr and then poured into 50 ml of water. The dark reaction product was extracted with ethyl acetate and purified by chromatography over silica gel (heptane/ethyl acetate as eluent), to provide 380 mg of 17 as a brown solid; $R_f$ 0.38 (hept./ethyl ac. 6/4), $R_f$ (starting material) 0.44. NMR (DMSO) 3.85, 3.92 (2×s, 6H, $OCH_3$) 4.03 (s, 2H, $CH_2$), 7.03, 7.30, 8.13, 8.38 (2×AB, 4H, Ar—H), 7.25, 7.61 (2×br.s, 2H, Ar—H).

Compound 18

To a solution of 900 mg of 17 in 8 ml of pyridine was added at 0° C. 700 μl of trifluoromethanesulphonic anhydride. Stirring was performed for 1 hr at RT followed by pouring into water and additional stirring for 15 min. followed by filtration of the crude product. Purification was achieved by chromatography over silicagel, to provide 800 mg of triflate 18; Mp 165-168° C. NMR ($CDCl_3$) 3.90, 3.96 (2×s, 6H, $OCH_3$), 4.18 (s, 2H, $CH_2$), 7.0, 7.09, 7.29, 7.35, 8.11, 8.47 (6H, Ar—H).

Compound 19

A mixture of 210 mg of triflate 18, 220 mg of 3-hydroxyphenyl-pinacolborane, 200 mg of $K_3PO_4$, 15 mg of $As(PPh)_3$, 15 mg of $PdCl_2.PPh_3$, 0.5 ml of water and 5 ml of dioxane was heated at 100° C. for 1.5 hr under a nitrogen atmosphere. The reaction was poured into water and extracted with ethyl acetate. Chromatography of the resulting material provided 215 mg of 19 as an amorphous product; $R_f$ 0.35 (hept./ethyl ac. 7/3), Mp 184-185° C. NMR ($CDCl_3$) 3.74, 3.87 (s, 6H, $OCH_3$), 3.80 (s, 2H, $CH_2$), 6.82-7.0 (m, 6H, Ar—H), 7.25, 7.40, 8.38, 8.53 (4H, Ar—H).

Compound 20

A mixture of 200 mg of 19, 500 mg of powdered K2CO3, 1.25 ml of 1,3-dibromopropane and 10 ml of acetonitrile was heated at 55° C. for 3 hr. The reaction was diluted with water and extracted with ethyl acetate. The crude product was purified by chromatography on silica gel (hept./ethyl acetate), to provide 220 mg of 20; $R_f$ 0.63 (hept./eth.ac. 7/3); NMR ($CDCl_3$) 3.65 (t, 2H, $CH_2Br$), 2.33 (m, 2H, $CH_2$), 4.13 (t, 2H, $CH_2O$), 3.78 (s, 2H, $CH_2$).

Compound 21

To a solution of 220 mg of 20 in 7 ml of methylenechloride was added 1.5 ml of $BF_3$.dimethylsulfde complex. The mixture was stirred until completion of the reaction (5 hr). The reaction was poured into water and the product extracted with ethyl acetate. Chromatography provided 210 mg of 21 as a colorless amorphous material; $R_f$ 0.25 (hept./eth.ac. 7/3). NMR ($CDCl_3$) 3.67 (t, 2H, $CH_2Br$), 2.33 (m, 2H, $CH_2$), 4.15 (t, 2H, $CH_2O$), 3.77 (s, 2H, $CH_2$).

Compound 22

A mixture of 70 mg of 21, 0.3 ml of 1,2,5,6-tetrahydropyridine and 3 ml of acetonitrile was heated at 55° C. for ½ hr. The mixture was then poured onto 5% $NaHCO_3$ and extracted with ethyl acetate. The product was purified by passing through a short silica column ($CH_2Cl_2/CH_3OH$). The product thus obtained was converted into a HCl salt by treatment of a solution the free base in methanol/ether with 1M HCl/ether. The hydrochloride salt thus obtained was freeze-dried from water to obtain 45 mg of amorphous 22. NMR (DMSO) 9.77, 9.82 (2×s, 2H, OH's), 5.70 and 5.88 (2×m, 2H, tetrahydropyridine), 8.32, 8.20, 7.52, 7.21, 7.08, 6.98, 6.87 (10, aromatic H's).

Example 6

Scheme 8

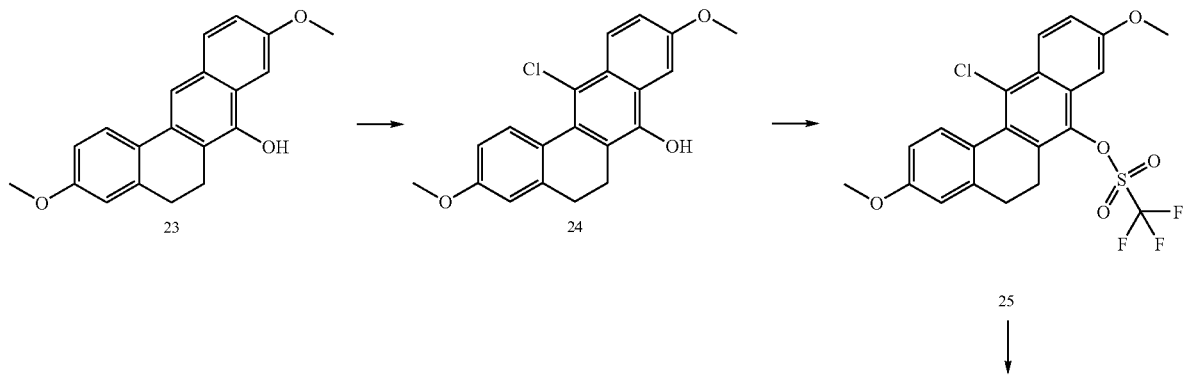

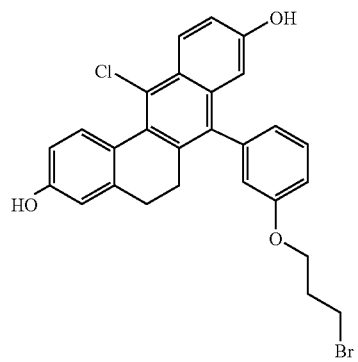

28

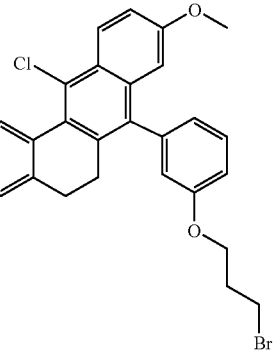

27

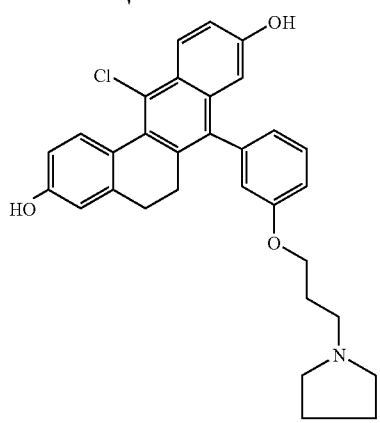

26

29

3,9dimethoxy-7-hydroxy-5,6-dihydro-benz[a]anthracene (compounds 23) and 12chloro-3,9-dimethoxy-7-hydroxy-5,6-dihydro-benz[a]anthracene (compound 24)

The compound 3,9-dimethoxy-7-hydroxy-5,6-dihydro-benz[a]anthracene (compounds 23) was prepared analogously to compound 16 in example 5. To a solution of 600 mg of 23 in 10 ml of DMF was added in portions 600 mg of 2,3,4,4,5,6-hexachlorocyclohexa-2,5-dien-1-one. The mixture was then stirred at 40° C. for 4 hr. Then the reaction was poured into water and the product extracted with ethyl acetate. The crude material was passed through a silicagel column (hept./eth.ac.) and finally triturated with heptane-diisopropyl ether to provide 280 mg of 24 as orange crystals; Mp 140-141° C., $R_f$ 0.28 (hept./eth.ac. 7/3) starting material $R_f$ 0.30.

Compound 25

To a solution of 300 mg of 24 in 3 ml of pyridine was added 200 μl of triflic anhydride. The mixture was stirred for 1 hr at rt, and then poured into water and extracted with ethyl acetate. The product was purified over silica gel and afforded 220 mg of 25 as a white solid; Mp 122-124; $R_f$ 0.70 (hept./ethyl ac. 7/3).

Compound 26

A mixture of 210 mg of 25, 220 mg of 3-hydroxyphenylpinacolborane, 200 mg of $K_3PO_4$ 15 mg of (PPh$_3$)As, 15 mg of PdCl$_2$(PPh$_3$)$_2$, 0.5 ml of water and 5 ml of dioxane was heated at 100° C. for 1.5 hr. The mixture was then poured into water and extracted with ethyl acetate. Chromatography over silica gel provided 215 mg of 26 as an oil; $R_f$ 0.28 (hept./ethyl acetate 7/3). NMR (DMSO) 2.56 (4H, CH$_2$CH$_2$), 3.67, 3.80 (2×s, 6H, OCH$_3$), 8.32, 8.18, 7.33, 6.93, 6.70 (10H, Ar—H's), 9.64 (s, 1H, OH).

Compound 27

A mixture of 215 mg of 26, 500 mg of $K_2CO_3$, 1.2 ml of 1,3-dibromopropane and 10 ml of acetonitrile was heated at 55° C. for 2.5 hr. The reaction was then poured in water and extracted with ethyl acetate. Chromatography provided 220 mg of 27 as a colorless oil; $R_f$ 0.60 (hept./ethyl acetate 7/3). NMR (CDCl$_3$) 2.60 (m, 4H, CH$_2$CH$_2$), 2.30 (m, 2H, CH$_2$), 3.60 (t, 2, CH$_2$Br), 4.13 (t, 2H, CH$_2$O), 3.72, 3.87 (2×s, 6H, OCH3).

Compound 28

To a solution of 190 mg of 27 in 7 ml of methylenechloride was added 1.5 ml of BF$_3$.dimethylsulfide complex. After stirring at rt for 4 hr the mixture was poured onto water and extracted with ethyl acetate. Chromatography of the crude product gave 150 mg of essentially pure 28; $R_f$ 0.20

(hept./ethyl ac. 7/3); NMR (DMSO) 2.27 (m, 2H, CH$_2$), 2.50 (m, 4H, CH$_2$CH$_2$), 3.68 (t, 2H, CH$_2$Br), 4.12 (t, 2H, CH$_2$O), 9.68, 9.82 (2×s, 2, OH).

Compound 29

A mixture of 60 mg of 28, 0.4 ml of pyrrolidine and 3 ml of acetonitrile was stirred at 50° C. for ½ hr. The mixture was then poured into 5% NaHCO3 and extracted with ethyl acetate. The product was purified by passing through a short silica column (CH$_2$Cl$_2$/CH$_3$OH as eluent) and then converted into a HCl salt by treatment with 1M HCl/ether. The resulting hydrochloride was freeze dried from water to give 35 mg of 29; R$_f$ 0.20 (CH$_2$Cl$_2$/CH$_3$OH/HOAc 90/10/1); NMR (DMSO) 9.70 and 9.82 (2×s, 2H, OH's), 8.22, 8.05, 7.48 7.17, 7.06, 6.88, 6.84, 6.76, 6.70, 6.62 (m, 10H, Ar—H's), 4.10 (t, 2H, CH$_2$O).

Example 7 crude product was purified by chromatography on silica gel (hept./ethyl acetate), to provide 310 mg of 30; R$_f$ 0.50 (hept./eth.ac. 7/3); NMR (CDCl$_3$) 3.67 (t, 2H, CH$_2$Br), 4.35 (t, 2H, CH$_2$O), 3.79 (s, 2H, CH$_2$), 3.75, 3.87 (2×s, 6H, OCH$_3$).

Compound 31

To a solution of 310 mg of 30 in 6 ml of methylenechloride was added 2 ml of BF$_3$.dimethylsulfide complex. The mixture was stirred until completion of the reaction (5 hr). The reaction was poured into water and the product extracted with ethyl acetate. Chromatography provided 290 mg of 31 as a colorless amorphous material; R$_f$ 0.19 (hept./eth.ac. 7/3). NMR (CDCl$_3$) 3.67 (t, 2H, CH$_2$Br),), 4.35 (t, 2H, CH$_2$O), 3.76 (s, 2H, CH$_2$).

Compound 32

A mixture of 60 mg of 31 0.3 g of 2-pyrimidinylpiperazine and 2 ml of acetontrile was heated at 50° C. for 16 hr.

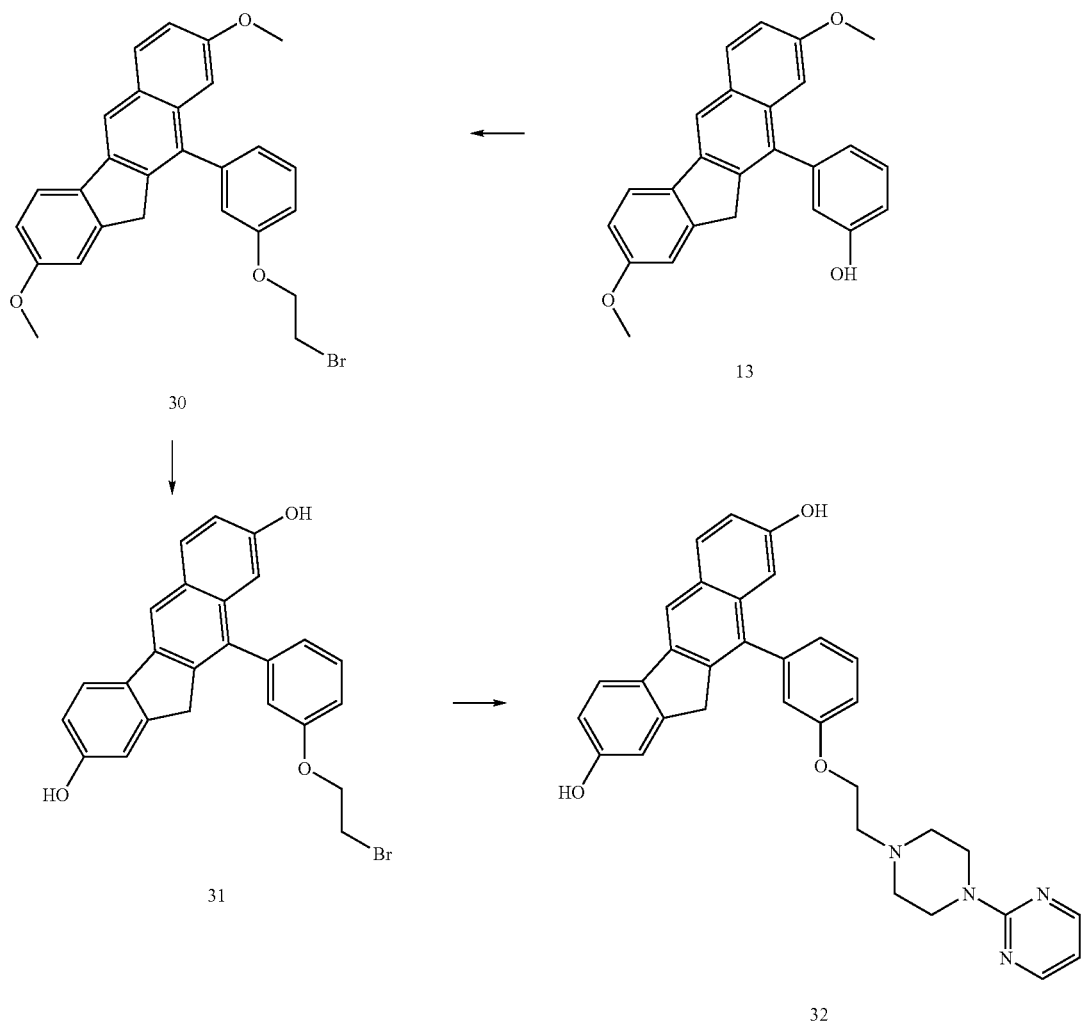

Compound 30

A mixture of 300 mg of compound 13, 900 mg of powdered K$_2$CO$_3$, 2 ml of 1,2-dibromopropane and 8 ml of acetonitrile was heated at 55° C. for 16 hr. The reaction was diluted with water and extracted with ethyl acetate. S The The mixture was then diluted with water and the product extracted with ethyl acetate. The organic material was passed through a short silica column (a gradient of CH$_2$Cl$_2$/CH$_3$OH as eluent), to provide essentially pure 32 as the free base. This was dissolved in a small amount of ethyl acetate and treated 25 with 1M HCl in ether to give the HCl salt. This was freeze dried from water to provide 48 mg of amorphous HCl salt of 32. $R_f$ 0.82 ($CH_2Cl_2$—$CH_3OH$—acetic acid 9/1/0,1); NMR (DMSO) 4.50 (m, 2H, $CH_2O$), 6.76, 6.84, 6.88, 6.96, 7.05, 7.09, 7.16, 7.21, 7.55, 8.21, 8.32, 8.44 (resp. 1H, 1H, 1H, 1H, 1H, 1H, 1H, 1H, 1H, 1H, 1H, 2H's; Ar—H's).

Example 8

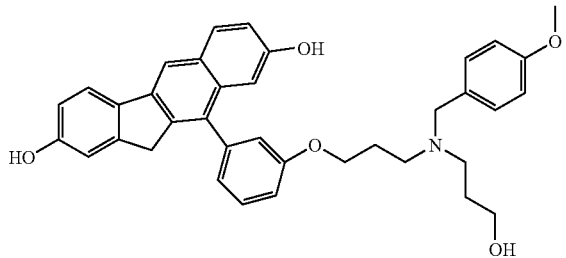

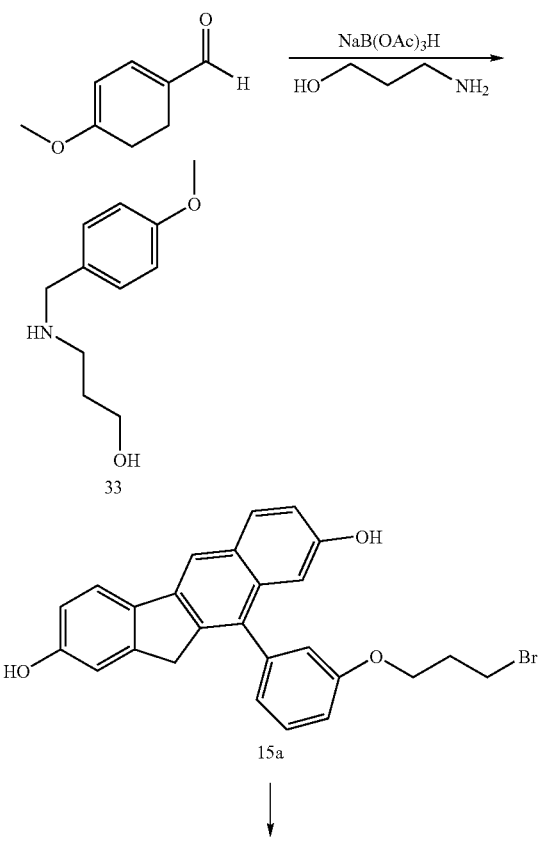

Compound 33

To 610 mg of NaBH4 in 20 ml of THF was added dropwise 2.7 ml of acetic acid. The mixture was allowed to stirr for 1 hr. A mixture of 1 ml of p-methoxybenzaldehyde and 3-amino-propanol in 2 ml of THF was stirred for ½ hr and then added to the aforementioned hydride solution. This was stirred overnight. The reaction was poured into water and acidified with 2N HCl. The acidic phase was washed with ethyl acetate and then treated with 2N NaOH to make the mixture slightly basic. Extraction with ethyl acetate, followed by washing, drying and concentration provided 880 mg of 33; NMR ($CDCl_3$) δ 6.88 and 7.23 (AB, 4H, Ar—H's); 1.72 (m, 2H), 2.90 (m, 2H), 3.74 (s, 2, $ArCH_2N$—), 3.82 (s and d, 5H, $OCH_3$ and $CH_2OH$)

Compound 34

A mixture of 120 mg of 15a and 250 mg of 33 in 2 ml of acetonitrile was heated at 60° C. for 16 hr. The reaction was poured into 5% $NaHCO_3$ and extracted with ethyl acetate. The product was purified by passing through a short silica column (dichloromethane-methanol). The product thus obtained was taken up in 2 ml of ether and treated with 1 eq of 1M HCl in ether. The precipitate was isolated by centrifugation of the supernatant and dissolved in water and freeze dried, to give 110 mg of 34.

NMR δ (DMSO) 9.50 (2×s, phenolic OH's), 1.87 (m, 2H), 2.20 (m, 2H), 3.08 (m, 2H), 3.18 (m, 2H), 3,46 (m, 2H) 4.21 (m, 2H), 3.68 (m, 2H), 3.70 (s, 3H, $OCH_3$) 4.10 (m, 2H); $R_f$ 0.43 (dichloromethane/methanol 9/1).

Example 9

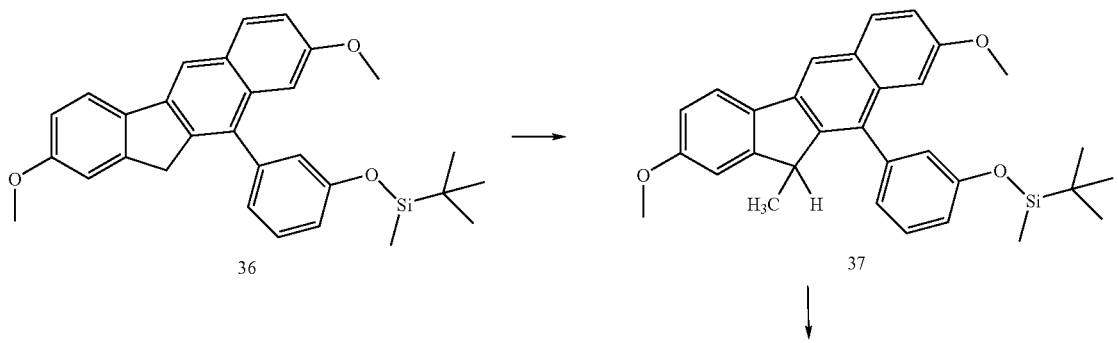

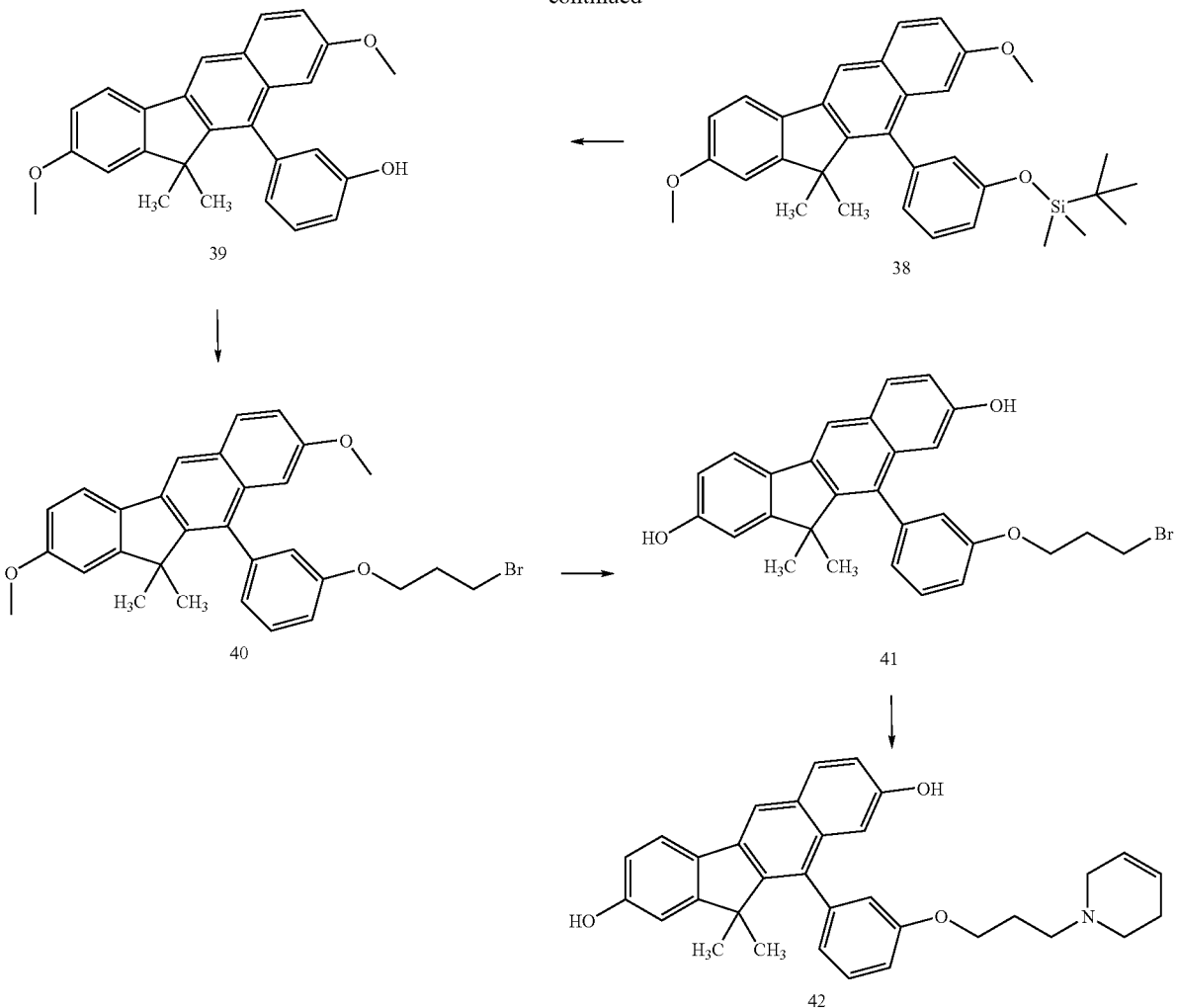

Compound 37

To a solution of 3 gr of silylether protected phenol 36 in 25 ml of dry THF (under N₂) was added at –20° C., 12.5 ml of 1M of LiHMDS solution in THF. The blue reaction mixture was stirred for an additional 45 min, after which period 1 ml of methyliodide was added The mixture was stirred for an additional ½ hr and then poured onto 100 ml of water and extracted with ethyl acetate. After washing, drying and concentration 3.2 gr of 37 were isolated as amorphous solid in essentially pure form; NMR (CDCl₃): δ 0.22 (d, 6H, (CH₃)₂—Si), 1.01(s, 9H, tBuSi), 1.03(d, 3H, CHCH₃), 3.71 and 3.73 (3H, 2×OCH3 rotamers) 3.87 and 3.88 (3H, 2×OCH3 rotamers), 4.15 (m, 1H, CH(CH₃)) 6.92-8.0 (11 Ar—H's); TLC: R_f 0.69 (hept/ethyl acetate 7/3, the same value as the starting material).

Compound 38

A solution of 600 mg of 37 in 5 ml of dry THF was treated with 1 ml of 1.6M BuLi in hexane at –60° C. The reaction mixture was stirred for 1 hr at –30° C. and then treated with 1 ml of methyliodide. The mixture was stirred for ½ hr at –30° C. and then warmed to room temperature and quenched by addition of water. The product was extracted with ethyl acetate and the organic phase was washed, dried and concentrated, to provide 580 mg of 38 in essentially pure form; R_f 0,70 (hept/ethyl acetate 7/3). (NMR (CDCl₃): δ 0.20 (2s, 6H, (CH₃)₂—Si); 0.98(s, 9H, (CH₃)₃Si), 1.34 (2×s, 6H, C(CH₃)₂), 3.63 (s, 3H, OCH₃), 3.87(s, 3H, OCH₃)

Compound 39

To a solution of 600 mg of 38 in 2 ml of THF was added 1.6 ml of 1M +TBAF in THF. The mixture was stirred for 15 minutes and then treated with 25 ml of sat. NH₄Cl solution and extracted with ethyl acetate. The product thus obtained was purified by passing through a short silica column, to provide 400 mg of 39 as a white solid; Mp 198-200° C.; NMR (CDCl₃) δ 1.35 and 1.30 (2s, 6H, C(CH₃)₂), 3.66, 3.87(6H, 2×OCH3), 4.85 (broad s, OH); R_f 0.37 (hept/ethyl acetate 7/3).

Compound 40

A mixture of 350 mg of 39, 750 mg of dry K₂CO₃, 2.3 ml of 1,3-dibromopropane and 10 ml of acetonitrile was stirred at 60° C. for 3 hr. Then the reaction was poured into water and extracted with ethyl acetate. The material thus obtained was purified by chromatography, to give 440 mg of colorless oil; R_f 0.62 (hept/ethyl acetate 7/3). NMR (CDCl₃) δ 1.35 and 1.31 (2×s, 6H, C(CH$_3$)$_2$), 2.34 (m, 2H, —CH$_2$—), 3.62 (t, 2H, CH$_2$Br), 4.14 (t, 2H, CH$_2$O), 3.66, 3.88 (2×s, 6H, OCH$_3$).

Compound 41

A solution of 440 mg of 40 in 5 ml of dichloromethane was treated with 3.6 ml of BF$_3$.dimethylsulfide complex. The mixture was stirred overnight and then ice-water was added and the product extracted into methylenechloride. Purification was achieved by passing through a short silica column (heptane/ethyl acetate as eluent), to provide 280 mg of 41, Rf 0.19 (hept/ethyl acetate 7/3). NMR (CDCl$_3$)δ 1.33 and 1.30 (2×s, 6H, CH$_3$), 2.33 (m, 2H, —CH$_2$—), 3.62 (t, 3H, CH$_2$Br), 4.14 (m, 2H, CH$_2$O), 4.85 (broad s, 2H, OH's).

Compound 42

A solution of 65 mg of 41 in 1 ml of acetonitrile and 0.2 ml of 1,2,3,6-tetrahydropyridine was heated at 60° C. for 3 hr. The mixture was then poured into 10 ml of 5% aqueous NaHCO3 and extracted with ethyl acetate. The product was passed through a short silica column (using methylene-dichloride/methanol 95/5 as eluent). The purified material thus obtained was treated with one equivalent of 1M HCl in ether and the solid thus obtained was freeze dried from water to give 46 mg of 42 as HCl salt. R$_f$ 0.45 (CH$_2$Cl$_2$-methanol 9/1); NMR (DMSO) δ 9.43 and 9.53 (2s, 2H, OH's), 8.05 (s, 1, ArH), 7.78 (1H, ArH), 7.70 (1H, ArH)7.49 (t, 1H, ArH), 7.10 (dd, 1H, ArH) 7.02(dd, 1H, ArH), 6.88 (br s, 1H, ArH), 6.91 (d, 1H, ArH)6.78(2H, m, ArH's), 6.42(d, 1H, ArH), 5.71 and 5.90(2×br d, 2H, —CH═CH—), 1.23 (2s, 6H, CH$_3$).

Example 10

Biological Activity

Determination of competitive binding to cytoplasmic human estrogen receptor α or β from recombinant CHO cells is used to estimate the relative affinity (potency ratio) of a test compound for estrogen receptors present in the cytosol of recombinant Chinese hamster ovary (CHO) cells, stably transfected with the human estrogen receptor α (hER α) or β receptor (hERβ), as compared with 17β-estradiol (E$_2$).

The estrogenic and antiestrogenic activity of compounds is determined in an in vitro bioassay with recombinant Chinese hamster ovary (CHO) cells stably co-transfected with the human estrogen receptor α (hERα) or β receptor (hERβ), the rat oxytocin promoter (RO) and the luciferase reporter gene (LUC). The estrogenic activity (potency ratio) of a test compound to stimulate the transactivation of the enzyme luciferase mediated via the estrogen receptors hERα or hERβ is compared with the standard estrogen estradiol. The antiestrogenic activity (potency ratio) of a test compound to inhibit the transactivation of the enzyme luciferase mediated via the estrogen receptors hERα or hERβ by the estrogen estradiol is compared with the standard ICI 164.384 (=(7α, 17β)-N-butyl-3,17-dihydroxy-N-methyl-estra-1,3,5(10)-triene-7-undecanamide).

Results (Table on Next Page)

| Compound | ERβ antagonism |
|---|---|
| 5a | + |
| 5b | + |
| 5c | + |
| 5d | + |
| 5e | ++ |
| 5f | + |
| 5g | + |
| 5h | + |
| 5I | + |
| 5j | + |
| 5k | + |
| 5l | ++ |
| 5m | ++ |
| 5n | + |
| 5o | + |
| 5p | + |
| 5q | + |
| 5r | ++ |
| 5s | + |
| 5t | + |
| 5u | ++ |
| 5v | + |
| 7a | +++ |
| 7b | +++ |
| 7c | +++ |
| 7d | +++ |
| 7e | +++ |
| 9 | ++ |
| 12a | +++ |
| 12b | ++ |
| 12c | +++ |
| 12d | + |
| 14 | ++ |
| 17a | +++ |
| 17b | ++ |
| 17c | ++ |

>5% (relative to ICI): +
>40%: ++
>100%: +++

The invention claimed is:

1. A compound, or a pharmaceutically acceptable salt thereof, having the formula 1,

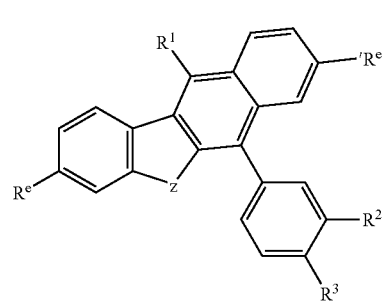

Formula 1 wherein:
R$^e$ and 'R$^e$ are OH, optionally independently etherified or esterified;
Z is —C(R$^4$,R$^5$)—, wherein R$^4$ and R$^5$ are independently (1C-2C)alkyl or form together a spiro(3C-5C)cycloalkyl;
R$^1$ is H, halogen, CF$_3$, or (1C-4C)alkyl;
R$^2$ and R$^3$ are independently H, halogen, —CF$_3$, —OCF$_3$, (1C-8C)alkyloxy, aryloxy, aryl(1C-8C)alkyl, halo(1C-8C)alkyl, —O(CH$_2$)$_m$X, wherein X is halogen or phenyl and m=2-4; —O(CH$_2$)$_m$NR$_a$R$_b$, —S(CH$_2$)$_m$NR$_a$R$_b$ or —(CH$_2$)$_m$NR$_a$R$_b$, wherein m=2-4 and wherein R$_a$, R$_b$ are independently (1C-8C)alkyl, (2C-8C)alkenyl, (2C-8C)alkynyl, or aryl, which alkyl, alkenyl and aryl can optionally be substituted with halogen, —CF$_3$, —OCF$_3$, —CN, —NO$_2$, —OH, (1C-8C)alkoxy, aryloxy, carboxyl, (1C-8C)alkylthio, carboxylate, (1C-8C)alkyl, aryl, aryl(1C-8C)alkyl or halo(1C-8C)alkyl; or R$_a$ and R$_b$ form a 3-8 membered ring structure, optionally substituted with halogen, —CF$_3$, —OCF$_3$, —CN, —NO$_2$, hydroxy, hydroxy(1C-4C)alkyl, (1C-8C)alkoxy, aryloxy, (1C-8C)alkylthio, carboxyl, carboxylate, (1C-8C)alkyl, aryl, aryl(1C-8C)alkyl, halo(1C-8C)alkyl.

2. The compound, or a pharmaceutically acceptable salt thereof, according to claim 1, wherein R$^3$ is H and R$^2$ is —O(CH$_2$)$_m$NR$_a$R$_b$, —S(CH$_2$)$_m$NR$_a$R$_b$ or —(CH$_2$)$_m$NR$_a$R$_b$, wherein m=2-4 and wherein R$_a$, R$_b$ are independently (1C-8C)alkyl, (2C-8C)alkenyl, (2C-8C)alkynyl, or aryl, which alkyl, alkenyl and aryl can be optionally substituted with halogen, —CF$_3$, —OCF$_3$, —CN, —NO$_2$, —OH, (1C-8C)alkoxy, aryloxy, carboxyl, (1C-8C)alkylthio, carboxylate, (1C-8C)alkyl, aryl, aryl(1C-8C)alkyl or halo(1C-8C)alkyl; or R$_a$ and R$_b$ form a 3-8 membered ring structure, optionally substituted with halogen, —CF$_3$, —OCF$_3$, —CN, —NO$_2$, hydroxy, hydroxy(1C-4C)alkyl, (1C-8C)alkoxy, aryloxy, (1C-8C)alkylthio, carboxyl, carboxylate, (1C-8C)alkyl, aryl, aryl(1C-8C)alkyl, halo(1C-8C)alkyl.

3. The compound according to claim 1, wherein R$^1$ is selected from H, halogen and CF$_3$.

4. The compound according to claim 2, wherein,
R$^2$ is —O(CH$_2$)$_m$NR$_a$R$_b$, wherein m=2-3 and R$_a$, R$_b$ are independently (1C-5C)alkyl, (3C-5C)alkenyl, or aryl, which alkyl, alkenyl and aryl can be optionally substituted with OH or methoxy, or R$_a$ and R$_b$ form a 4-7 membered ring structure selected from the list: azetidine, pyrrolidine, 3-pyrroline, piperidine, piperazine, tetrahydropyridine, morpholine, thiomorpholine, thiazolidine, homopiperidine, tetrahydroquinoline and 6-azabicyclor[3.2.1]octane, which 4-7 membered ring structure can optionally be substituted with OH, methoxy, acetyl, carboxylate, (1C-3C)alkyl, phenyl, benzyl, and phenylethyl.

5. A method of treating an estrogen receptor related disorder selected from the group consisting of contraception, benign prostate hypertrophy, osteoporosis, Alzheimer's disease and depression, comprising administering an effective amount of the compound according to claim 1 to a patient in need thereof.

6. A pharmaceutical composition, comprising:
the compound of claim 1, and
a pharmaceutically acceptable carrier.

7. The method of claim 5, wherein the estrogen receptor related treatment is contraception.

8. The method of claim 5, wherein the estrogen receptor related treatment is treatment of benign prostate hypertrophy.

9. The method of claim 5, wherein the estrogen receptor related treatment is treatment of osteoporosis.

10. The method of claim 5, wherein the estrogen receptor related treatment is treatment of Alzheimer's disease.

11. The method of claim 5, wherein the estrogen receptor related treatment is treatment of depression.

* * * * *

UNITED STATES PATENT AND TRADEMARK OFFICE
CERTIFICATE OF CORRECTION

PATENT NO. : 7,335,659 B2
APPLICATION NO. : 10/505631
DATED : February 26, 2008
INVENTOR(S) : Hubert Jan Jozef Loozen et al.

It is certified that error appears in the above-identified patent and that said Letters Patent is hereby corrected as shown below:

Claim 1, col. 32 line 62 to col. 33 line 11:

$R^2$ and $R^3$ are independently H, halogen, -$CF_3$, -$OCF_3$, (1C-8C)alkyloxy, aryloxy, aryl(1C-8C)alkyl, halo(1C-8C)alkyl, -$O(CH_2)_m$,X, wherein X is halogen or phenyl and m = 2-4; -$O(CH_2)_mNR_aR_b$, -$S(CH_2)_mNR_aR_b$ or -$(CH_2)_mNR_aR_b$, wherein m = 2-4 and wherein $R_a$, $R_b$ are independently (1C-8C)alkyl, (2C-8C)alkenyl, (2C-8C) alkynyl, or aryl, which alkyl, alkenyl and aryl can optionally be substituted with halogen, -$CF_3$, -$OCF_3$, -CN, -$NO_2$, -OH, (1C-8C)alkoxy, aryloxy, carboxyl, (1C-8C)alkylthio, carboxylate, (1C-8C)alkyl, aryl, aryl(1C-8C)alkyl or halo(1C-8C)alkyl; or $R_a$ and $R_b$ form a 3-8 membered ring structure, optionally substituted with halogen, -$CF_3$, - $OCF_3$, -CN, -$NO_2$, hydroxy, hydroxy(1C-4C)alkyl, (1C- 8C)alkoxy, aryloxy, (1C-8C)alkylthio, carboxyl, carboxylate, (1C-8C)alkyl, aryl, aryl(1C-8C)alkyl, halo(1 C-8C)alkyl.

should read

$R^2$ and $R^3$ are independently H, halogen, -$CF_3$, -$OCF_3$, (1C-8C)alkyl, hydroxy, (1C-8C)alkyloxy, aryloxy, aryl(1C-8C)alkyl, halo(1C-8C)alkyl, -$O(CH_2)_m$,X, wherein X is halogen or phenyl and m = 2-4; -$O(CH_2)_mNR_aR_b$, -$S(CH_2)_mNR_aR_b$ or -$(CH_2)_mNR_aR_b$, wherein m = 2-4 and wherein $R_a$, $R_b$ are independently (1C-8C)alkyl, (2C-8C)alkenyl, (2C-8C)alkynyl, or aryl, which alkyl, alkenyl and aryl can optionally be substituted with halogen, -$CF_3$, -$OCF_3$, -CN, -$NO_2$, -OH, (1C-8C)alkoxy, aryloxy, carboxyl, (1C-8C)alkylthio, carboxylate, (1C-8C)alkyl, aryl, aryl(1C-8C)alkyl or halo(1C-8C)alkyl; or $R_a$ and $R_b$ form a 3-8 membered ring structure, optionally substituted with halogen, -$CF_3$, -$OCF_3$, -CN, -$NO_2$, hydroxy, hydroxy(1C-4C)alkyl, (1C-8C)alkoxy, aryloxy, (1C-8C)alkylthio,

UNITED STATES PATENT AND TRADEMARK OFFICE
CERTIFICATE OF CORRECTION

PATENT NO.       : 7,335,659 B2                                             Page 2 of 2
APPLICATION NO.  : 10/505631
DATED            : February 26, 2008
INVENTOR(S)      : Hubert Jan Jozef Loozen et al.

It is certified that error appears in the above-identified patent and that said Letters Patent is hereby corrected as shown below:

carboxyl, carboxylate, (1C-8C)alkyl, aryl, aryl(1C-8C)alkyl, halo(1 C-8C)alkyl.

Signed and Sealed this

Twenty-fourth Day of June, 2008

JON W. DUDAS
*Director of the United States Patent and Trademark Office*